(12) United States Patent
Ye

(10) Patent No.: US 9,266,817 B2
(45) Date of Patent: Feb. 23, 2016

(54) CATECHOLAMINE DERIVATIVES FOR OBESITY AND NEUROLOGICAL DISORDERS

(71) Applicant: EMORY UNIVERSITY, Atlanta, GA (US)

(72) Inventor: Keqiang Ye, Lilburn, GA (US)

(73) Assignee: Emory University, Atlanta, GA (US)

( * ) Notice: Subject to any disclaimer, the term of this patent is extended or adjusted under 35 U.S.C. 154(b) by 0 days.

(21) Appl. No.: 14/336,911

(22) Filed: Jul. 21, 2014

(65) Prior Publication Data
US 2014/0329907 A1 Nov. 6, 2014

Related U.S. Application Data

(62) Division of application No. 13/256,250, filed as application No. PCT/US2010/027588 on Mar. 17, 2010, now abandoned.

(60) Provisional application No. 61/161,911, filed on Mar. 20, 2009.

(51) Int. Cl.
| | |
|---|---|
| A61K 31/05 | (2006.01) |
| A61K 31/12 | (2006.01) |
| A61K 31/133 | (2006.01) |
| A61K 31/135 | (2006.01) |
| C07C 225/16 | (2006.01) |
| C07C 215/60 | (2006.01) |
| C07C 237/20 | (2006.01) |
| A61K 31/137 | (2006.01) |

(52) U.S. Cl.
CPC ............ *C07C 225/16* (2013.01); *A61K 31/05* (2013.01); *A61K 31/12* (2013.01); *A61K 31/133* (2013.01); *A61K 31/135* (2013.01); *A61K 31/137* (2013.01); *C07C 215/60* (2013.01); *C07C 237/20* (2013.01)

(58) Field of Classification Search
CPC ..... A61K 31/05; A61K 31/12; A61K 31/133; A61K 31/135
See application file for complete search history.

(56) References Cited

U.S. PATENT DOCUMENTS 5,232,923 A * 8/1993 Fukazawa et al. ......... 514/237.5

FOREIGN PATENT DOCUMENTS

| WO | 2007-109882 | 10/2007 |
| WO | 2008-092257 | 8/2008 |

OTHER PUBLICATIONS

Arevalo et al. TrkA Immunoglobulin-Like Ligand Binding Domains Inhibit Spontaneous Activation of the Receptor Molecular and Cellular Biology, 2000, p. 5908-5916.
Chen et al. A Chemical-Genetic Approach to Studying Neurotrophin Signaling Neuron, 2005, vol. 46, 13-21.
Chhatwal et al. Identification of cell-type-specific promoters within the brain using lentiviral vectors, Gene Therapy (2007) 14, 575-583.
Chhatwal et al. Amygdala BDNF signaling is required for consolidation but not encoding of extinction, Nature Neuroscience, 2006 9(7):870.
Dias et al. Differential regulation of Brain Derived Neurotrophic Factor transcripts by antidepressant treatments in the adult rat brain, Neuropharmacology 45 (2003) 553-563.
Garza et al. Exercise, antidepressant treatment, and BDNF mRNA expression in the aging brain, Pharmacology, Biochemistry and Behavior 77 (2004) 209-220.
Ivy et al. Noradrenergic and serotonergic blockade inhibits BDNF mRNA activation following exercise and antidepressant, Pharmacology, Biochemistry and Behavior 75 (2003) 81-88.
Rajagopal et al. Transactivation of Trk Neurotrophin Receptors by G-Protein-Coupled Receptor Ligands Occurs on Intracellular Membranes The Journal of Neuroscience, Jul. 28, 2004 • 24(30):6650-6658.
Rios et al. Conditional Deletion of Brain-Derived Neurotrophic Factor in the Postnatal Brain Leads to Obesity and Hyperactivity, Molecular Endocrinology 15(10):1748-1757.
Siuciak et al. Antidepressant-Like Effect of Brain-derived Neurotrophic Factor (BDNF), Pharmacology Biochemistry and Behavior, vol. 56, No. 1, pp. 131-137, 1997.
Purushottamachar et al. First pharmacophore-based identification of androgen receptor down-regulating agents: Discovery of potent antiprostate cancer agents, Bioorganic & Medicinal Chemistry 15 (2007) 3413-3421.
Sakkas et al. Heterogeneous photocatalytic degradation of the pharmaceutical agent salbutamol in aqueous titanium dioxide suspensions, Applied Catalysis B: Environmental 77 (2007) 135-144.
Goodwin et al Metabolism of Phenylethanolamines and 2-Oxo-2-Phenylethylamines in the Rat, Gen. Pharmac. vol. 28, No. 4, pp. 535-543, 1997.
Joyce et al. Loss of Dopamine D2 Receptors in Alzheimer's Disease with Parkinsonism But Not Parkinson's or Alzheimer's Disease, Neuropsychopharmacology (1998) 19, 472-480.
Peskind et al. Cerebrospinal Fluid Epinephrine in Alzheimer's Disease and Normal Aging, Neuropsychopharmacology (1998) 19, 465-471.
Sweet et al. Catechol-O-methyltransferase haplotypes are associated with psychosis in Alzheimer disease, Molecular Psychiatry (2005) 10, 1026-1036.
Lui et al., Norepinephrine Protects against Amyloid-β Toxicity via TrkB. J Alzheimers Dis. 2015;44(1):251-60.
Umegaki et al. The metabolism of plasma glucose and catecholamines in Alzheimer's disease, Experimental Gerontology 35 (2000) 1373±1382.

* cited by examiner

*Primary Examiner* — Yong Chong
(74) *Attorney, Agent, or Firm* — Emory Patent Group

(57) ABSTRACT

Novel compounds, compositions, and methods related to the activation of the TrkB receptor are provided. The methods include administering in vivo or in vitro a therapeutically effective amount of a compound containing a catecholamine backbone and pharmaceutically acceptable salts, prodrugs, and derivatives thereof. Specifically, methods, compositions, and compounds for the treatment of disorders including neurological disorders, neuropsychiatric disorders, and metabolic disorders are provided. For example, a first method is provided of treating or reducing the risk of depression, anxiety, or obesity in a subject, which includes administering to the subject a therapeutically effective amount of the described compounds. A further method of promoting neuroprotection in a subject also is provided, which includes administering to the subject a therapeutically effective amount of the described compounds.

1 Claim, 16 Drawing Sheets

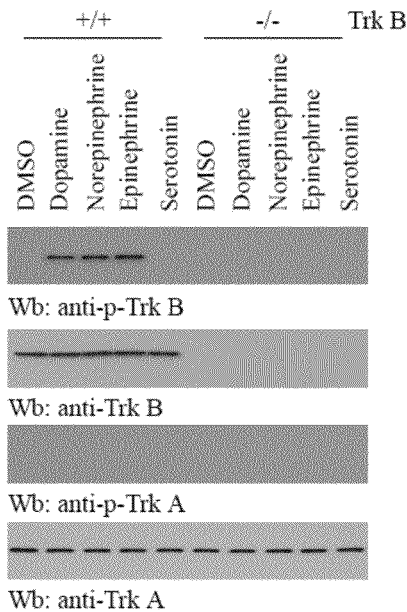
Fig. 15A
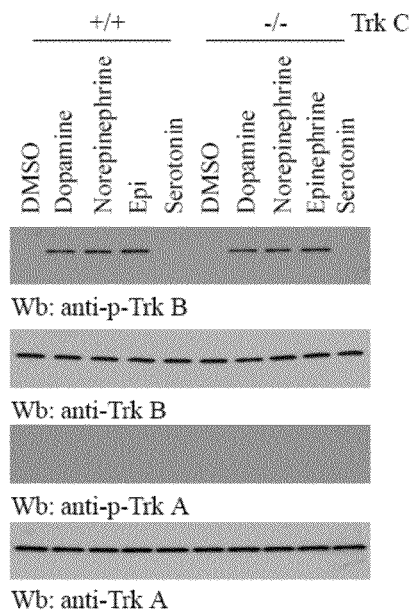
Fig. 15B
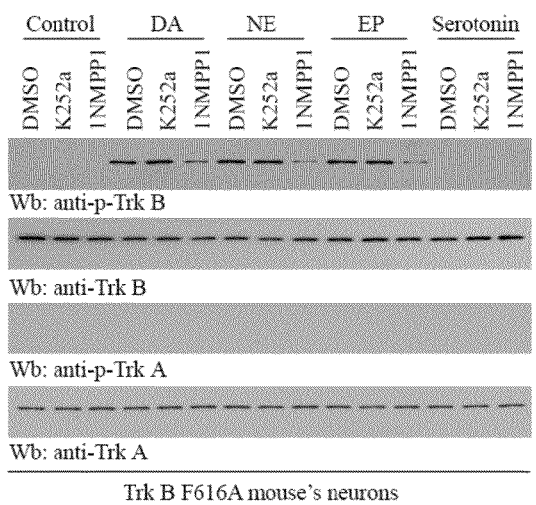
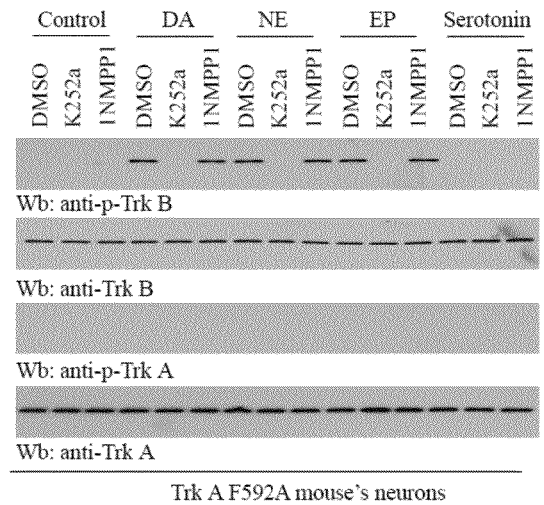
Fig. 16

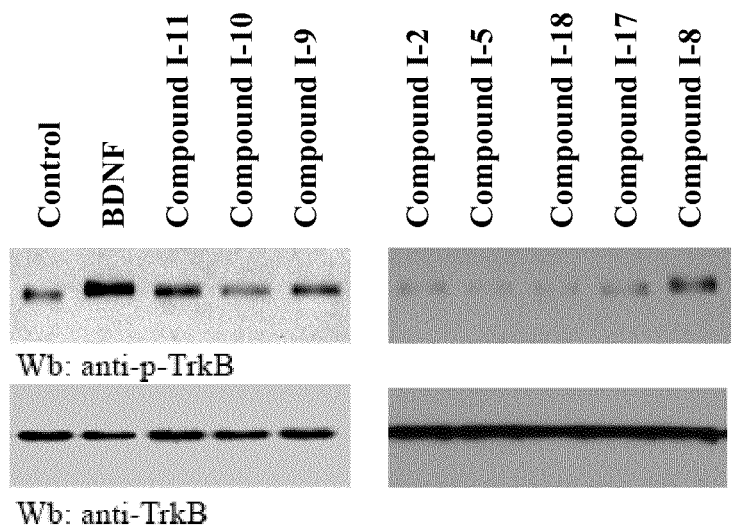
Fig. 23
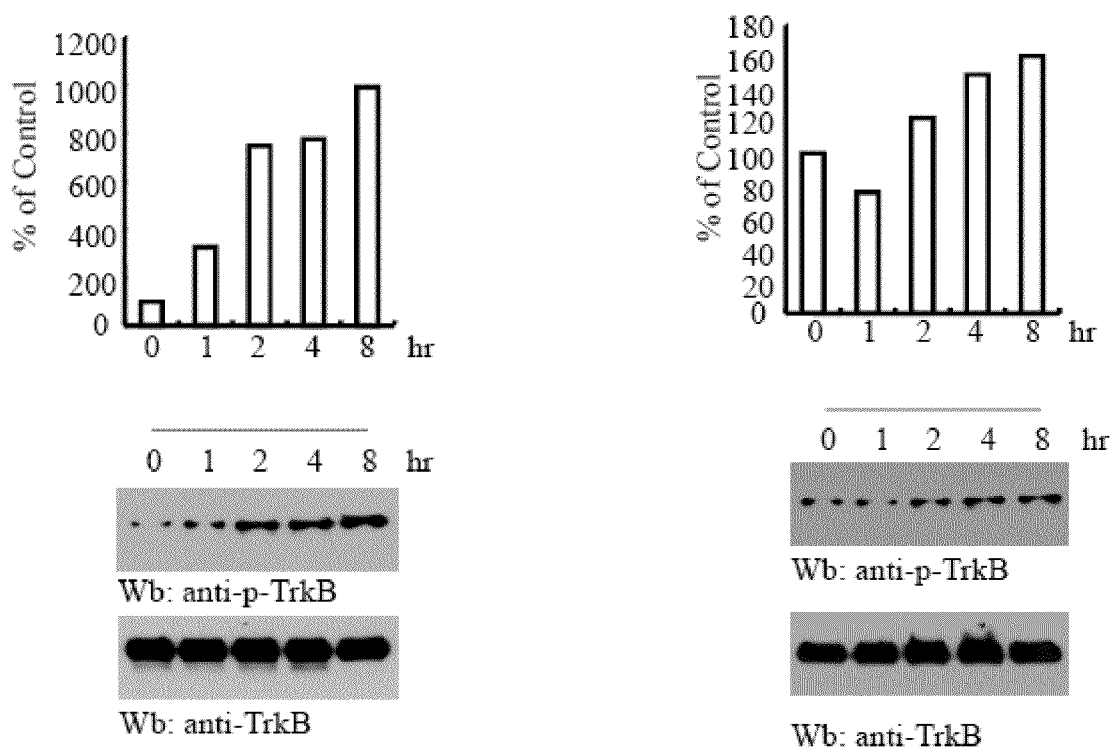
Fig. 24A
Fig. 24B

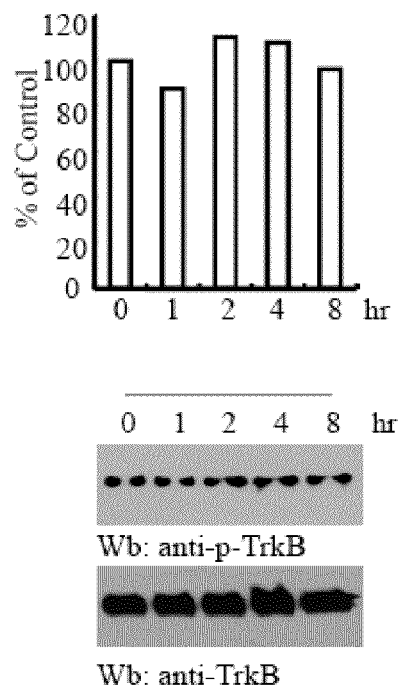
Fig. 24C
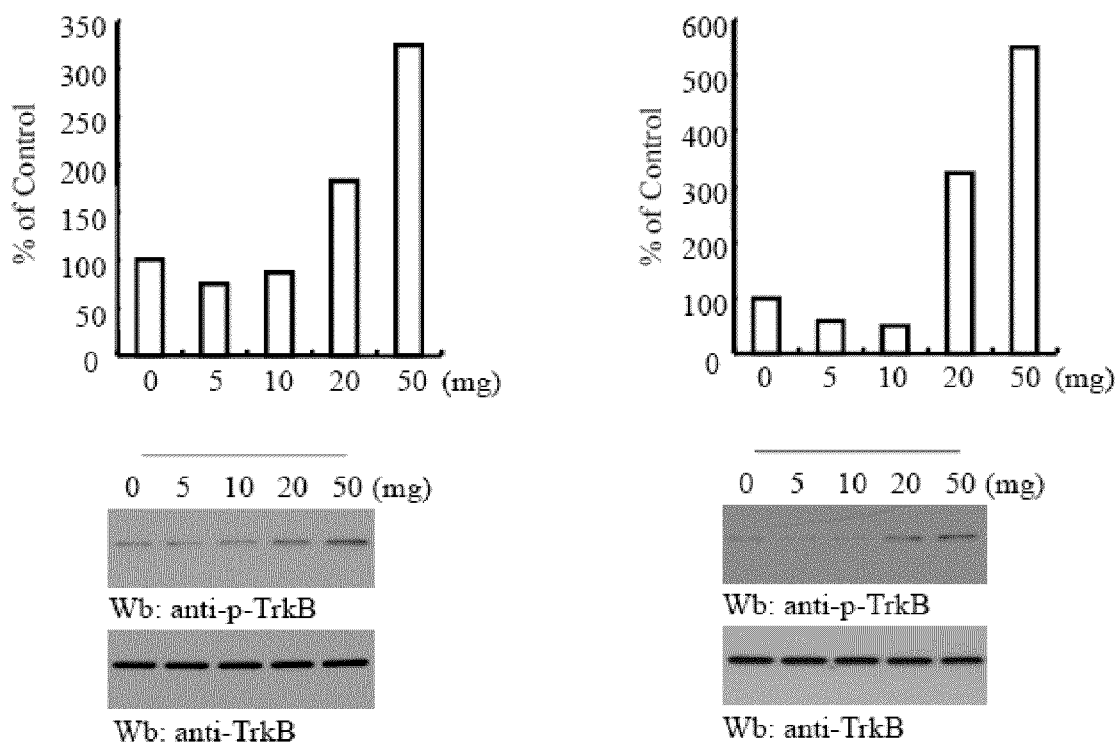
Fig. 25A                    Fig. 25B

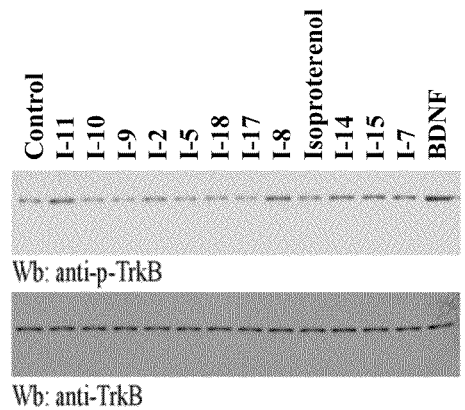
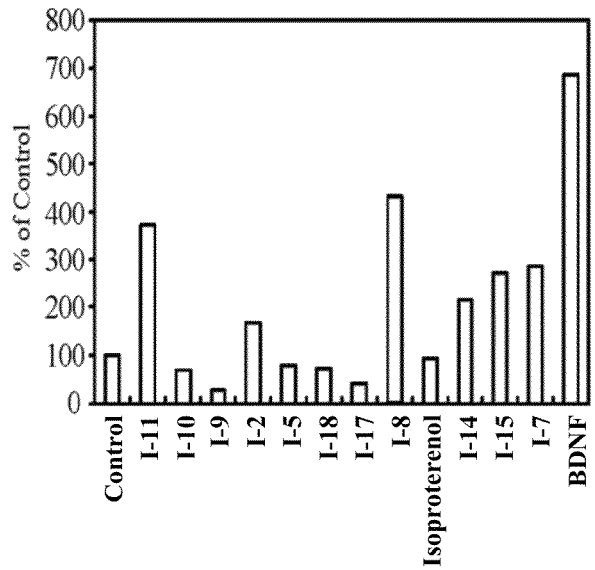
Fig. 26A
Fig. 26B
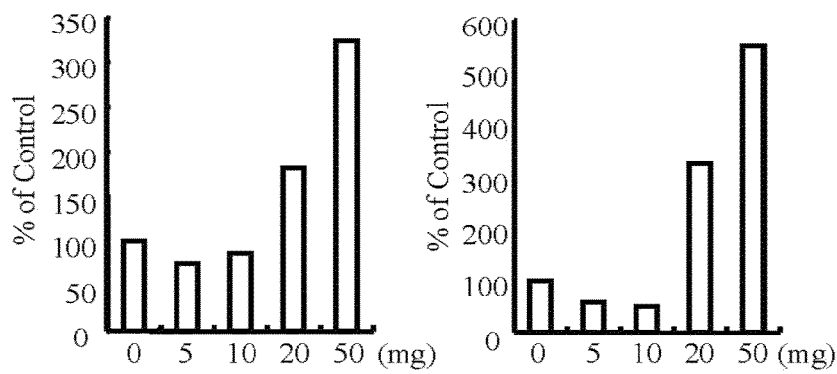
Compound I-11
Wb: anti-p-TrkB
Wb: anti-TrkB
Compound I-8
Wb: anti-p-TrkB
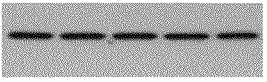
Wb: anti-TrkB
Fig. 27A

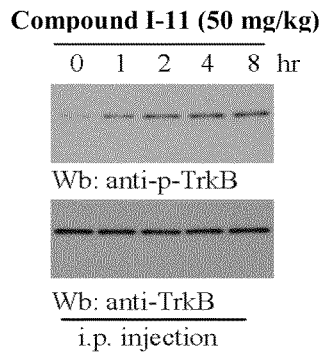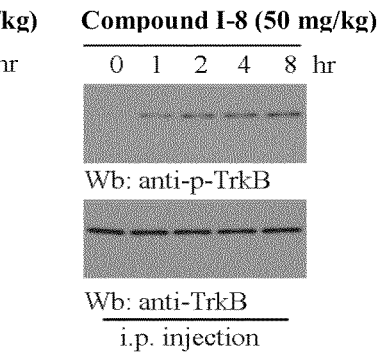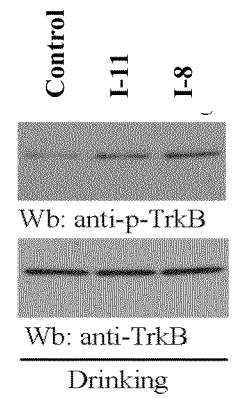
Fig. 27B            Fig. 27C
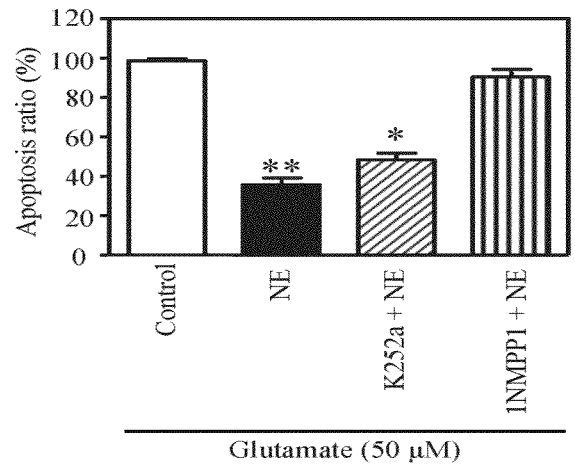
Fig. 28A
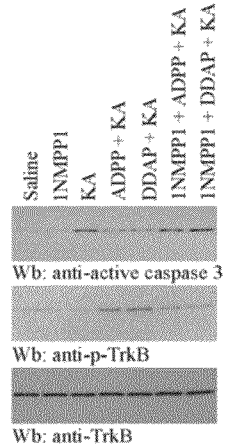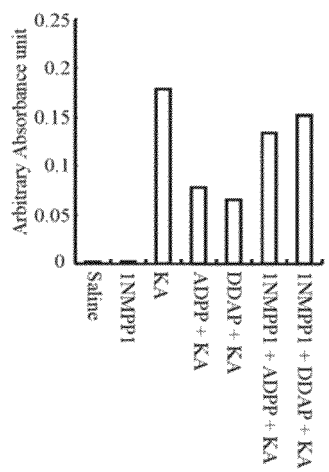
Fig. 28B

F.S.T.

US 9,266,817 B2

CATECHOLAMINE DERIVATIVES FOR OBESITY AND NEUROLOGICAL DISORDERS

CROSS-REFERENCE TO PRIORITY APPLICATIONS

This application is a divisional of and claims priority to pending U.S. patent application Ser. No. 13/256,250 filed the 13 Sep. 2011, PCT application Number PCT/US10/27588 filed 17 Mar. 2010, and U.S. Provisional Application No. 61/161,911, filed 20 Mar. 2009, which are all incorporated herein by reference in their entirety.

STATEMENT REGARDING FEDERALLY FUNDED RESEARCH

This invention was made with government support under Grant No. R01NS045627, awarded by the National Institutes of Health. The government has certain rights in the invention.

BACKGROUND

Neurologic and neuropsychiatric disorders such as depression, anxiety, amyotrophic lateral sclerosis, and central nervous system injuries, to name a few, afflict millions of people every year and result in a multitude of symptoms including weight change, decreased energy, headaches, digestive problems, chronic pain, paralysis, and in certain instances, death. Neurotrophins, such as brain-derived neurotrophic factor (BDNF), affect various neuronal populations involved in neurologic, neuropsychiatric, and metabolic disorders. Neurotrophins like BDNF are natural ligands of tyrosine kinase receptor TrkB. TrkB is activated in hippocampal neurons prior to BDNF expression by norepinephrine, which is a type of catecholamine.

SUMMARY

Novel compounds and methods for the treatment of disorders including neurological disorders, neuropsychiatric disorders (e.g., depression or anxiety), and metabolic disorders (e.g., obesity) are provided. The methods include administering to a subject a therapeutically effective amount of a compound having the following formula:

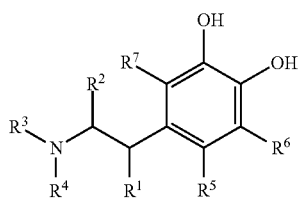

or a pharmaceutically acceptable salt or prodrug thereof. In this compound, $R^1$ is hydrogen, —OH, or =O; $R^2$ is hydrogen, substituted or unsubstituted $C_{1-4}$ alkyl, substituted or unsubstituted $C_{1-4}$ heteroalkyl, substituted or unsubstituted $C_{2-4}$ alkenyl, substituted or unsubstituted $C_{2-4}$ heteroalkenyl, substituted or unsubstituted $C_{2-4}$ alkynyl, substituted or unsubstituted $C_{2-4}$ heteroalkynyl, or substituted or unsubstituted carbonyl; $R^3$ and $R^4$ are each independently selected from hydrogen, substituted or unsubstituted $C_{1-12}$ alkyl, substituted or unsubstituted $C_{3-12}$ cycloalkyl, substituted or unsubstituted $C_{1-12}$ heteroalkyl, substituted or unsubstituted $C_{2-12}$ alkenyl, substituted or unsubstituted $C_{3-12}$ cycloalkenyl, substituted or unsubstituted $C_{2-12}$ heteroalkenyl, substituted or unsubstituted $C_{2-12}$ alkynyl, substituted or unsubstituted $C_{3-12}$ cycloalkynyl, substituted or unsubstituted $C_{2-12}$ heteroalkynyl, substituted or unsubstituted carbonyl; and $R^5$, $R^6$, and $R^7$ are each independently selected from hydrogen, halogen, —OH, or alkoxy, wherein one of $R^1$, $R^2$, $R^3$, $R^4$, $R^5$, $R^6$, or $R^7$ is not hydrogen; wherein if one of $R^3$ or $R^4$ is a saccharide, $R^5$ is not hydrogen; wherein if $R^1$ is —OH, one of $R^2$, $R^3$, $R^4$, $R^5$, $R^6$, or $R^7$ is not hydrogen; if $R^1$ is —OH and one of $R^3$ or $R^4$ is —CH$_3$, one of $R^2$, $R^3$, $R^4$, $R^5$, $R^6$, or $R^7$ is not hydrogen; if $R^2$ is —COOH, one of $R^1$, $R^3$, $R^4$, $R^5$, $R^6$, or $R^7$ is not hydrogen; and if $R^2$ is —COOH and $R^1$ is —OH, then one of $R^3$, $R^4$, $R^5$, $R^6$, or $R^7$ is not hydrogen. In some examples, if $R^1$ is —OH and one of $R^3$ or $R^4$ is isopropyl, one of $R^2$, $R^3$, $R^4$, $R^5$, $R^6$, or $R^7$ is not hydrogen.

A method for the treatment of disorders including neurological disorders, neuropsychiatric disorders, and metabolic disorders using these compounds is related to treating or reducing the risk of depression, anxiety, or obesity in a subject, which includes administering to the subject a therapeutically effective amount of the compound described above or a derivative thereof. A method of promoting neuroprotection in a subject also is provided, which includes administering to the subject a therapeutically effective amount of the compound described above or a derivative thereof.

A method of activating a TrkB receptor on a neuron also is provided. The method includes providing a neuron having a TrkB receptor, and contacting the TrkB receptor in vitro or in vivo with a compound as described above or a derivative thereof in an amount sufficient to activate the TrkB receptor. The neuron can be, for example, a mammalian cell.

Also provided herein are novel compositions including the compounds described herein or derivatives thereof and an anti-depressant or an anti-anxiolytic. Methods of making the compounds described herein are also provided in which L-DOPA or L-DOPS are used as starting materials.

The details of one or more examples of the compounds, compositions, and methods are set forth in the accompanying drawings and the description below. Other features, objects, and advantages will be apparent from the description and drawings, and from the claims.

DESCRIPTION OF DRAWINGS

FIG. 7A illustrates that the catecholamines selectively bind the ICD but not the ECD of TrkB receptor, and 7,8-dihydroxylflavone binds the ECD but not the ICD of TrkB receptor. FIG. 7B includes a Scatchard plot analysis of these data indicating the binding constants of the catecholamines.

FIGS. 15A and 15B show Western blots indicating that catecholamines selectively activate TrkB receptors in cortical neurons. In FIG. 15A, catecholamines activated TrkB in wild-type but not TrkB-null neurons. In FIG. 15B, catecholamines induced TrkB activation in both wild-type and TrkC knockout neurons.

FIG. 16 shows Western blots illustrating that catecholamines activate cortical neurons with a TrkB F616A mutant. Catecholamines-provoked TrkB phosphorylation was selectively blocked by 1NMPP1 but not K252a, while serotonin had no effect (left panel). Catecholamines-induced TrkB activation was robustly inhibited by K252a but not by 1NMPP1 in TrkA F592A neurons (right panel).

FIG. 23 shows Western blots illustrating that catecholamine derivatives activate TrkB in primary cortical neurons.

FIGS. 24A, 24B, and 24C show Western blots illustrating that catecholamine derivatives (Compound I-11 and Compound I-8) activate TrkB orally. FIG. 24A shows the immunoblot results for Compound I-11. FIG. 24B shows the immunoblot results for Compound I-8. FIG. 24C shows the immunoblot results for Compound I-2.

FIGS. 25A and 25B show Western blots illustrating that catecholamine derivatives activated TrkB in a dose-dependent manner. FIG. 25A shows the immunoblot results for Compound I-11. FIG. 25B shows the immunoblot results for Compound I-8.

FIGS. 26A and 26B show Western blots illustrating that catecholamine derivatives activate TrkB in primary cortical neurons.

FIGS. 27A, 27B, and 27C show Western blots illustrating that catecholamine derivatives (Compound I-11 and Compound I-8) are orally bioavailable. FIG. 27A shows the immunoblot results for oral administration. FIG. 27B shows the immunoblot results for intraperitoneal injection. FIG. 27C shows the immunoblot results for the compounds dissolved in drinking water.

FIGS. 28A and 28B show graphs and Western blots illustrating that Compound I-11 and Compound I-8 suppress neuronal apoptosis in a TrkB dependent manner. FIG. 28A shows that norepinephrine blocks glutamate-provoked neuronal cell death in a TrkB dependent manner. FIG. 28B shows that Compounds I-11 and I-8 protect neurons from KA-induced apoptosis.

FIG. 29A shows that the swimming immobility of mice treated with Compounds I-11 and I-8 was decreased. FIG. 29B shows the swimming immobility of TrkB F616 knockin mice treated with Compounds I-11 and I-8 after pretreatment with saline or 1NMPP1.

DETAILED DESCRIPTION

Figure 1:
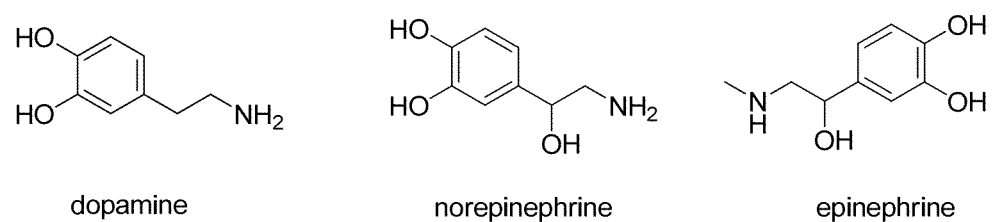
FIG. 1 shows the chemical structures of several catecholamines.

Described herein are compounds, compositions, and methods for the activation of a TrkB receptor. These compounds, compositions, and methods are effective in the treatment of diseases and illnesses associated with the activation of the TrkB receptor including neurological disorders, neuropsychiatric disorders, and metabolic disorders. Examples of neurological disorders include depression, anxiety, Alzheimer's disease, central nervous system (CNS) injuries, and the like. Examples of metabolic disorders include obesity and hyperphagia. Specifically, provided herein are compounds containing a catecholamine backbone and pharmaceutically acceptable salts, prodrugs, and derivatives thereof. Methods of their use in the treatment of neurological disorders, neuropsychiatric disorders, and obesity are also described herein.

The compounds containing a catecholamine backbone as described herein are represented by Compound I:

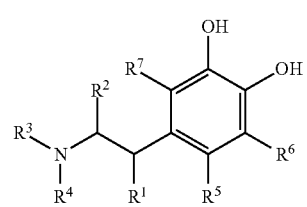

and pharmaceutically acceptable salts and prodrugs thereof.

In Compound I, $R^1$ is hydrogen, —OH, or =O.

Also, in Compound I, $R^2$ is hydrogen, substituted or unsubstituted $C_{1-4}$ alkyl, substituted or unsubstituted $C_{1-4}$ heteroalkyl, substituted or unsubstituted $C_{2-4}$ alkenyl, substituted or unsubstituted $C_{2-4}$ heteroalkenyl, substituted or unsubstituted $C_{2-4}$ alkynyl, or substituted or unsubstituted $C_{2-4}$ heteroalkynyl, or substituted or unsubstituted carbonyl. $R^2$ can be, for example,

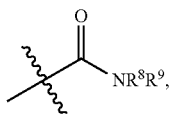

wherein $R^8$ and $R^9$ are each independently selected from hydrogen, substituted or unsubstituted $C_{1-4}$ alkyl, substituted or unsubstituted $C_{2-4}$ alkenyl, or substituted or unsubstituted $C_{2-4}$ alkynyl. As an example, $R^2$ can be

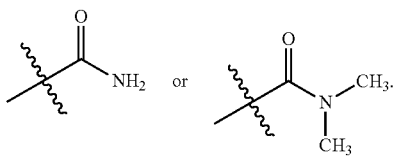

Additionally, in Compound I, $R^3$ and $R^4$ are each independently selected from hydrogen, substituted or unsubstituted $C_{1-12}$ alkyl, substituted or unsubstituted $C_{3-12}$ cycloalkyl, substituted or unsubstituted $C_{1-12}$ heteroalkyl, substituted or unsubstituted $C_{2-12}$ alkenyl, substituted or unsubstituted $C_{3-12}$ cycloalkenyl, substituted or unsubstituted $C_{2-12}$ heteroalkenyl, substituted or unsubstituted $C_{2-12}$ alkynyl, substituted or unsubstituted $C_{3-12}$ cycloalkynyl, substituted or unsubstituted $C_{2-12}$ heteroalkynyl, substituted or unsubstituted carbonyl.

Further, in Compound I, $R^5$, $R^6$, and $R^7$ are each independently selected from hydrogen, halogen, —OH, or alkoxy. $R^5$, $R^6$, and $R^7$ can each be, for example, fluorine.

In Compound I, one of $R^1$, $R^2$, $R^3$, $R^4$, $R^5$, $R^6$, or $R^7$ is not hydrogen.

Also, in Compound I, if one of $R^3$ or $R^4$ is a saccharide, $R^5$ is not hydrogen.

Additionally, in Compound I, if $R^1$ is —OH, one of $R^2$, $R^3$, $R^4$, $R^5$, $R^6$, or $R^7$ is not hydrogen, or if $R^1$ is —OH and one of $R^3$ or $R^4$ is —CH$_3$, one of $R^2$, $R^3$, $R^4$, $R^5$, $R^6$, or $R^7$ is not hydrogen. In some examples, if $R^1$ is —OH and one of $R^3$ or $R^4$ is isopropyl, one of $R^2$, $R^3$, $R^4$, $R^5$, $R^6$, or $R^7$ is not hydrogen.

Further, in Compound I, if $R^2$ is —COOH, one of $R^1$, $R^3$, $R^4$, $R^5$, $R^6$, or $R^7$ is not hydrogen, or if $R^2$ is —COOH and $R^1$ is —OH, then one of $R^3$, $R^4$, $R^5$, $R^6$, or $R^7$ is not hydrogen.

In Compound I, $R^2$ and $NR^4$ can combine to form a substituted or unsubstituted heterocycloalkyl or a substituted or unsubstituted heteroaryl. In the combination of $R^2$ and $NR^4$, the substituted or unsubstituted heteroaryl is other than a pyrrole. For example, $R^2$ can be n-butane and $NR^4$ can be methanamine that combine to form a piperidine. Similarly, $R^3$ and $NR^4$ can combine to form a substituted or unsubstituted heterocycloalkyl or a substituted or unsubstituted heteroaryl.

Specific examples of Compound I are as follows:

I-1

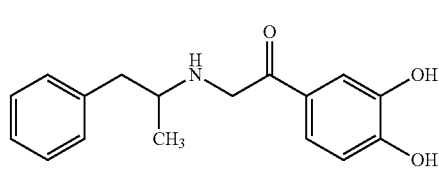

I-2

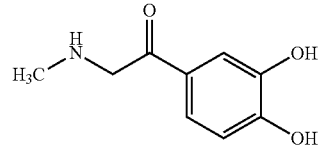

I-3

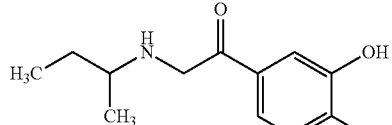

I-4

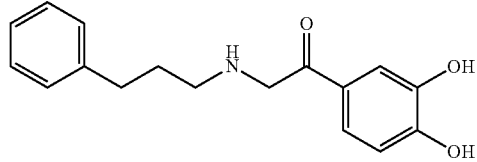

I-5

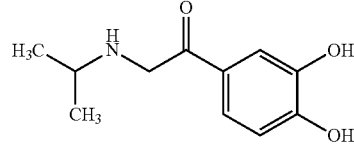

I-6

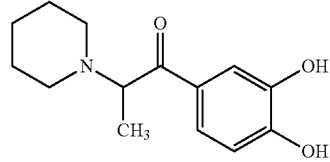

I-7

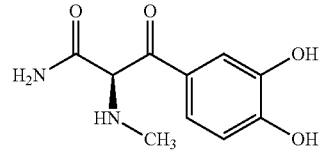

I-8

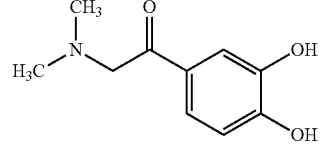

I-9

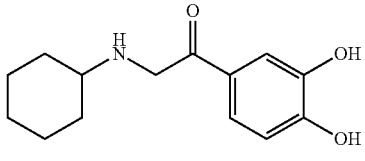

I-10

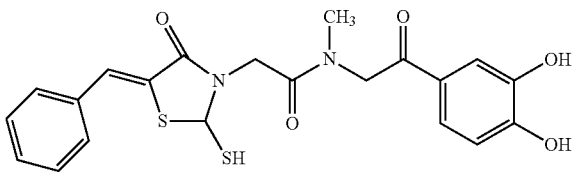

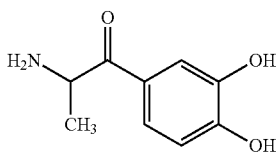

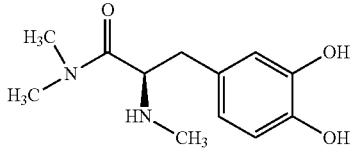

The compounds described herein can be prepared in a variety of ways known to one skilled in the art of organic synthesis or variations thereon as appreciated by those skilled in the art. The compounds described herein can be prepared from readily available starting materials. Optimum reaction conditions may vary with the particular reactants or solvents used, but such conditions can be determined by one skilled in the art.

Variations on Compound I include the addition, subtraction, or movement of the various constituents as described for each compound. Similarly, when one or more chiral centers is present in a molecule, the chirality of the molecule can be changed. Additionally, compound synthesis can involve the protection and deprotection of various chemical groups. The use of protection and deprotection, and the selection of appropriate protecting groups can be determined by one skilled in the art. The chemistry of protecting groups can be found, for example, in Wuts and Greene, Protective Groups in Organic Synthesis, 4th Ed., Wiley & Sons, 2006, which is incorporated herein by reference in its entirety.

As used herein, the terms alkyl, alkenyl, and alkynyl include straight- and branched-chain monovalent substituents. Examples include methyl, ethyl, isobutyl, 3-butynyl, and the like. Heteroalkyl, heteroalkenyl, and heteroalkynyl are similarly defined but may contain O, S, or N heteroatoms or combinations thereof within the backbone. The term substituted indicates the main substituent has attached to it one or more additional components, such as, for example, OH, halogen, or one of the substituents listed above.

Reactions to produce the compounds described herein can be carried out in solvents, which can be selected by one of skill in the art of organic synthesis. Solvents can be substantially nonreactive with the starting materials (reactants), the intermediates, or products under the conditions at which the reactions are carried out, i.e., temperature and pressure. Reactions can be carried out in one solvent or a mixture of more than one solvent. Product or intermediate formation can be monitored according to any suitable method known in the art. For example, product formation can be monitored by spectroscopic means, such as nuclear magnetic resonance spectroscopy (e.g., $^1H$ or $^{13}C$), infrared spectroscopy, spectrophotometry (e.g., UV-visible), or mass spectrometry, or by chromatography such as high performance liquid chromatography (HPLC) or thin layer chromatography.

The compounds described by Compound I and pharmaceutically acceptable salts and prodrugs thereof can be made, for example, using L-dihydroxyphenylserine (L-DOPS) or N-protected L-DOPS as a starting material. A method of making L-DOPS is shown in Scheme 1.

Scheme 1:

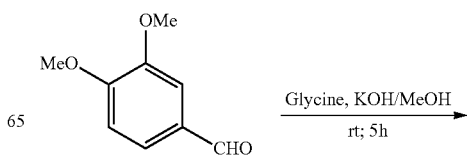

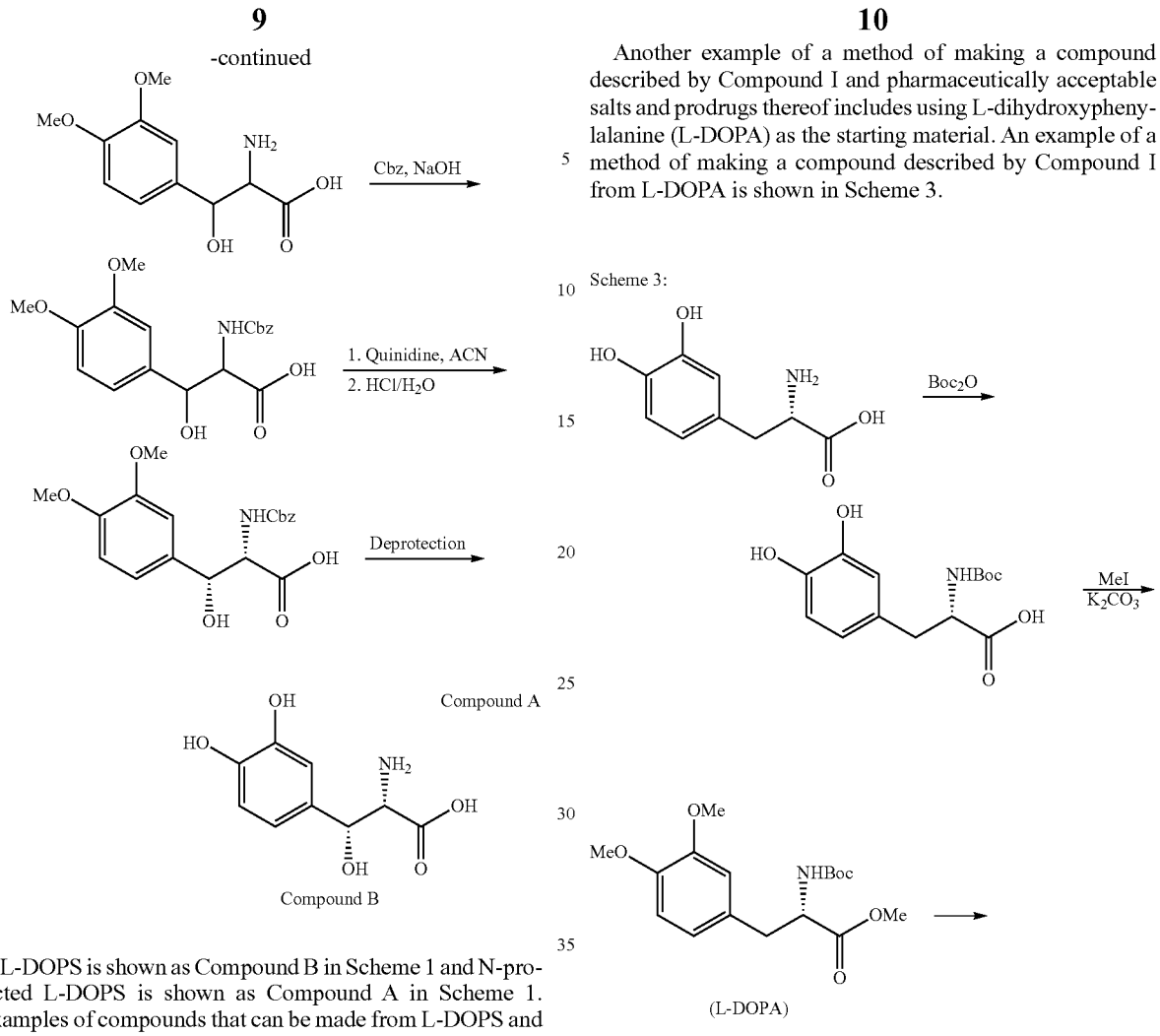

Another example of a method of making a compound described by Compound I and pharmaceutically acceptable salts and prodrugs thereof includes using L-dihydroxyphenylalanine (L-DOPA) as the starting material. An example of a method of making a compound described by Compound I from L-DOPA is shown in Scheme 3.

L-DOPS is shown as Compound B in Scheme 1 and N-protected L-DOPS is shown as Compound A in Scheme 1. Examples of compounds that can be made from L-DOPS and N-protected L-DOPS are shown in Scheme 2.

Scheme 2:

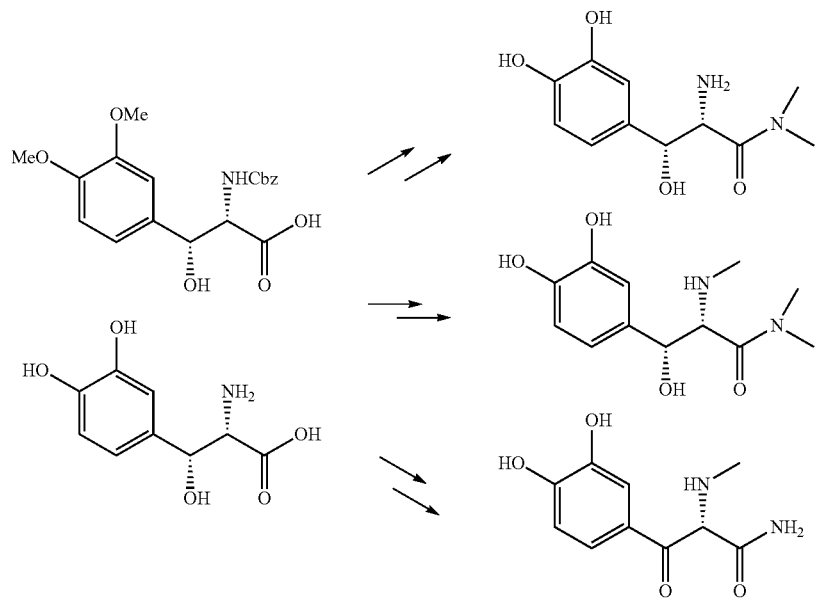

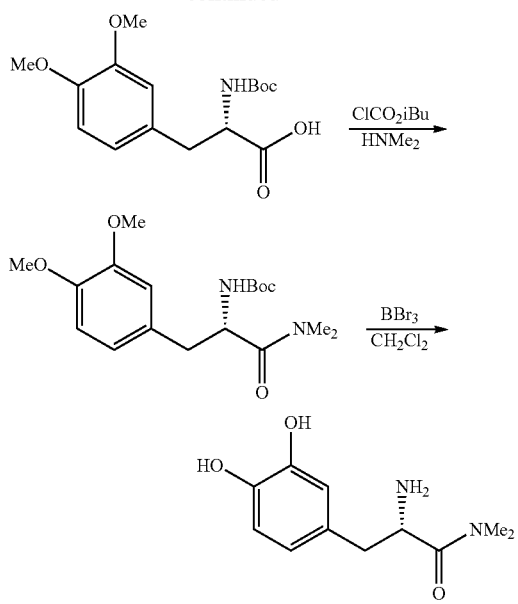

A further example of a method of making a compound described by Compound I and pharmaceutically acceptable salts and prodrugs thereof from L-DOPA is shown in Scheme 4.

Scheme 4:

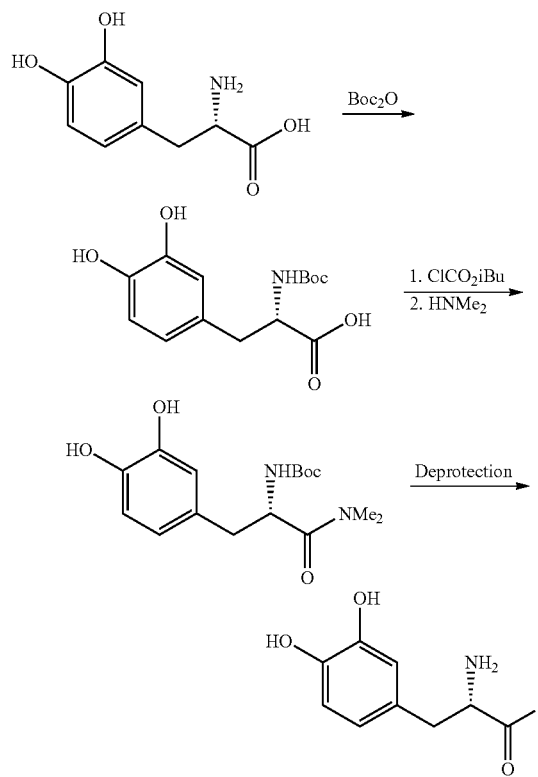

The compounds described herein by Compound I can be methylated at the primary amine to form N-methylated derivatives as shown in Scheme 5.

Scheme 5:

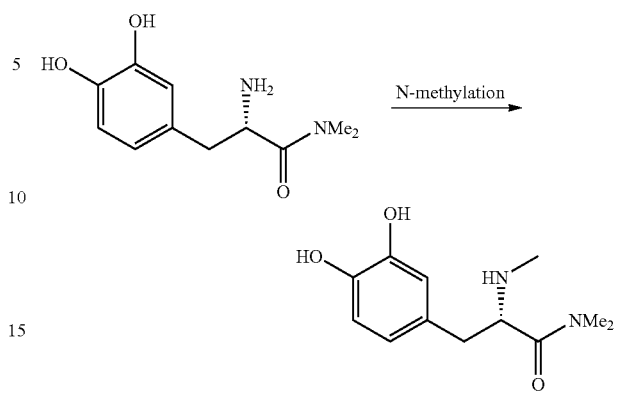

The methods described herein include a method of treating or reducing the risk of disorders associated with activation of the TrkB receptor including neurological disorders, neuropsychiatric disorders, and metabolic disorders in a subject by administering to the subject a therapeutically effective amount of Compound I or a derivative thereof. Examples of neurological and neuropsychiatric disorders include depression, anxiety, Alzheimer's disease, central nervous system (CNS) injuries, and the like. Examples of metabolic disorders include obesity and hyperphagia. This method optionally includes the step of selecting a subject with or at risk of developing the neurological disorder, neuropsychiatric disorder, or metabolic disorder (e.g., obesity). Compound I or a derivative thereof can be administered systemically (e.g., orally, parenterally (e.g., intravenously), intramuscularly, intraperitoneally, transdermally (e.g., by a patch), extracorporeally, topically, by inhalation, subcutaneously or the like), by administration into the central nervous system (e.g., into the brain (intracerebrally or intraventricularly), spinal cord, or into the cerebrospinal fluid), or any combination thereof.

Also provided is a method of promoting neuroprotection in a subject by administering to the subject a therapeutically effective amount of Compound I or derivative thereof as described herein. This method optionally includes the step of selecting a subject in need of neuroprotection. A subject in need of neuroprotection can, for example, be a subject that has or is at risk of developing a central nervous system disease (e.g., amyotrophic lateral sclerosis (ALS)) or a central nervous system injury. A central nervous system injury includes, for example, a brain injury, a spinal cord injury, a cerebrovascular event (e.g., a stroke), or a central nervous system surgery. Neuroprotection includes protecting neurons after injury or disease has occurred or before the onset of disease or injury.

The methods can further comprise testing the effectiveness of Compound I or derivative thereof as described herein. Testing the effectiveness can include, but is not limited to, imaging (e.g., Magnetic Resonance Imaging (MRI)) and functional measurements (e.g., survival or clinical symptoms like analysis of speech patterns, logic, comprehension, memory, mood, and orientation). The method optimally further comprises adjusting the dosage or treatment regimen of Compound I or derivative thereof as described herein.

Further provided is a method of activating a TrkB receptor on a neuron (e.g., a mammalian cell). This method includes the steps of providing a neuron having a TrkB receptor and contacting the TrkB receptor in vitro or in vivo with Compound I or a derivative thereof as described herein in an amount sufficient to activate the TrkB receptor. Also provided is a method of screening for an agent that potentiates TrkB receptor activation. The screening method includes activating the TrkB receptor on a neuron as described and contacting the neuron with the agent to be screened. An enhanced effect indicates the agent potentiates the effect of Compound I or derivative thereof as described herein.

The compounds described herein or derivatives thereof can be provided in a pharmaceutical composition. Depending on the intended mode of administration, the pharmaceutical composition can be in the form of solid, semi-solid or liquid dosage forms, such as, for example, tablets, suppositories, pills, capsules, powders, liquids, or suspensions, preferably in unit dosage form suitable for single administration of a precise dosage. The compositions include a therapeutically effective amount of the compounds described herein or derivatives thereof in combination with a pharmaceutically acceptable carrier and, in addition, may include other medicinal agents, pharmaceutical agents, carriers, or diluents. By pharmaceutically acceptable is meant a material that is not biologically or otherwise undesirable, which can be administered to an individual along with the selected compound without causing significant unacceptable biological effects or interacting in a deleterious manner with the other components of the pharmaceutical composition in which it is contained.

As used herein, the term carrier encompasses any excipient, diluent, filler, salt, buffer, stabilizer, solubilizer, lipid, stabilizer, or other material well known in the art for use in pharmaceutical formulations. The choice of a carrier for use in a composition will depend upon the intended route of administration for the composition. The preparation of pharmaceutically acceptable carriers and formulations containing these materials is described in, e.g., Remington: The Science and Practice of Pharmacy, 21st Edition, ed. University of the Sciences in Philadelphia, Lippincott, Williams & Wilkins, Philadelphia Pa., 2005. Examples of physiologically acceptable carriers include buffers such as phosphate buffers, citrate buffer, and buffers with other organic acids; antioxidants including ascorbic acid; low molecular weight (less than about 10 residues) polypeptides; proteins, such as serum albumin, gelatin, or immunoglobulins; hydrophilic polymers such as polyvinylpyrrolidone; amino acids such as glycine, glutamine, asparagine, arginine or lysine; monosaccharides, disaccharides, and other carbohydrates including glucose, mannose, or dextrins; chelating agents such as EDTA; sugar alcohols such as mannitol or sorbitol; salt-forming counterions such as sodium; and/or nonionic surfactants such as TWEEN® (ICI, Inc.; Bridgewater, N.J.), polyethylene glycol (PEG), and PLURONICS™ (BASF; Florham Park, N.J.).

Compositions containing Compound I or derivative thereof as described herein suitable for parenteral injection may comprise physiologically acceptable sterile aqueous or nonaqueous solutions, dispersions, suspensions or emulsions, and sterile powders for reconstitution into sterile injectable solutions or dispersions. Examples of suitable aqueous and nonaqueous carriers, diluents, solvents or vehicles include water, ethanol, polyols (propyleneglycol, polyethyleneglycol, glycerol, and the like), suitable mixtures thereof, vegetable oils (such as olive oil) and injectable organic esters such as ethyl oleate. Proper fluidity can be maintained, for example, by the use of a coating such as lecithin, by the maintenance of the required particle size in the case of dispersions and by the use of surfactants.

These compositions may also contain adjuvants such as preserving, wetting, emulsifying, and dispensing agents. Prevention of the action of microorganisms can be promoted by various antibacterial and antifungal agents, for example, parabens, chlorobutanol, phenol, sorbic acid, and the like. Isotonic agents, for example, sugars, sodium chloride, and the like may also be included. Prolonged absorption of the injectable pharmaceutical form can be brought about by the use of agents delaying absorption, for example, aluminum monostearate and gelatin.

Solid dosage forms for oral administration of Compound I or derivative thereof as described herein include capsules, tablets, pills, powders, and granules. In such solid dosage forms, the compounds described herein or derivatives thereof is admixed with at least one inert customary excipient (or carrier) such as sodium citrate or dicalcium phosphate or (a) fillers or extenders, as for example, starches, lactose, sucrose, glucose, mannitol, and silicic acid, (b) binders, as for example, carboxymethylcellulose, alignates, gelatin, polyvinylpyrrolidone, sucrose, and acacia, (c) humectants, as for example, glycerol, (d) disintegrating agents, as for example, agar-agar, calcium carbonate, potato or tapioca starch, alginic acid, certain complex silicates, and sodium carbonate, (e) solution retarders, as for example, paraffin, (f) absorption accelerators, as for example, quaternary ammonium compounds, (g) wetting agents, as for example, cetyl alcohol, and glycerol monostearate, (h) adsorbents, as for example, kaolin and bentonite, and (i) lubricants, as for example, talc, calcium stearate, magnesium stearate, solid polyethylene glycols, sodium lauryl sulfate, or mixtures thereof. In the case of capsules, tablets, and pills, the dosage forms may also comprise buffering agents.

Solid compositions of a similar type may also be employed as fillers in soft and hard-filled gelatin capsules using such excipients as lactose or milk sugar as well as high molecular weight polyethyleneglycols, and the like.

Solid dosage forms such as tablets, dragees, capsules, pills, and granules can be prepared with coatings and shells, such as enteric coatings and others known in the art. They may contain opacifying agents and can also be of such composition that they release the active compound or compounds in a certain part of the intestinal tract in a delayed manner. Examples of embedding compositions that can be used are polymeric substances and waxes. The active compounds can also be in micro-encapsulated form, if appropriate, with one or more of the above-mentioned excipients.

Liquid dosage forms for oral administration of Compound I or derivative thereof as described herein include pharmaceutically acceptable emulsions, solutions, suspensions, syrups, and elixirs. In addition to the active compounds, the liquid dosage forms may contain inert diluents commonly used in the art, such as water or other solvents, solubilizing agents, and emulsifiers, as for example, ethyl alcohol, isopropyl alcohol, ethyl carbonate, ethyl acetate, benzyl alcohol, benzyl benzoate, propyleneglycol, 1,3-butyleneglycol, dimethylformamide, oils, in particular, cottonseed oil, groundnut oil, corn germ oil, olive oil, castor oil, sesame oil, glycerol, tetrahydrofurfuryl alcohol, polyethyleneglycols, and fatty acid esters of sorbitan, or mixtures of these substances, and the like.

Besides such inert diluents, the composition can also include additional agents, such as wetting, emulsifying, suspending, sweetening, flavoring, or perfuming agents.

Suspensions, in addition to the active compounds, may contain additional agents, as for example, ethoxylated isostearyl alcohols, polyoxyethylene sorbitol and sorbitan esters, microcrystalline cellulose, aluminum metahydroxide, bentonite, agar-agar and tragacanth, or mixtures of these substances, and the like.

Compositions of the Compound I or derivative thereof as described herein for rectal administrations are optionally suppositories, which can be prepared by mixing the compounds with suitable non-irritating excipients or carriers such as cocoa butter, polyethyleneglycol or a suppository wax, which are solid at ordinary temperatures but liquid at body temperature and therefore, melt in the rectum or vaginal cavity and release the active component.

Dosage forms for topical administration of the compounds described herein or derivatives thereof include ointments, powders, sprays, and inhalants. The compounds described herein or derivatives thereof are admixed under sterile conditions with a physiologically acceptable carrier and any preservatives, buffers, or propellants as may be required. Ophthalmic formulations, ointments, powders, and solutions are also contemplated as being within the scope of the compositions.

The term pharmaceutically acceptable salt as used herein refers to those salts of Compound I or derivative thereof as described herein that are, within the scope of sound medical judgment, suitable for use in contact with the tissues of subjects without undue toxicity, irritation, allergic response, and the like, commensurate with a reasonable benefit/risk ratio, and effective for their intended use, as well as the zwitterionic forms, where possible, of the compounds described herein. The term salts refers to the relatively non-toxic, inorganic and organic acid addition salts of Compound I or derivative thereof as described herein. These salts can be prepared in situ during the isolation and purification of the compounds or by separately reacting the purified compound in its free base form with a suitable organic or inorganic acid and isolating the salt thus formed. Representative salts include the hydrobromide, hydrochloride, sulfate, bisulfate, nitrate, acetate, oxalate, valerate, oleate, palmitate, stearate, laurate, borate, benzoate, lactate, phosphate, tosylate, citrate, maleate, fumarate, succinate, tartrate, naphthylate mesylate, glucoheptonate, lactobionate, methanesulfonate, and laurylsulfonate salts, and the like. These may include cations based on the alkali and alkaline earth metals, such as sodium, lithium, potassium, calcium, magnesium, and the like, as well as non-toxic ammonium, quaternary ammonium, and amine cations including, but not limited to ammonium, tetramethylammonium, tetraethylammonium, methylamine, dimethylamine, trimethylamine, triethylamine, ethylamine, and the like. (See Stahl and Wermuth, Pharmaceutical Salts: Properties, Selection, and Use, Wiley VCH, 2008, which is incorporated herein by reference in its entirety, at least, for the compositions taught therein.)

The compounds described above or derivatives thereof are useful in treating or reducing the risk of disorders associated with activation of the TrkB receptor including neurological disorders, neuropsychiatric disorders, and metabolic disorders (e.g., obesity). As used herein, the terms treating (including treat and treatment) or reducing the risk of include prevention; delay in onset; diminution, eradication, or delay in exacerbation of one or more signs or symptoms after onset; and prevention of relapse.

Further, the compounds described above or derivatives thereof are useful for promoting neuroprotection in humans, e.g., including pediatric and geriatric populations, and in animals, e.g., veterinary applications. A subject in need of neuroprotection is a subject at risk for or having a neurological or neuropsychiatric disorder. Neurological or neuropsychiatric disorders include, for example, depression, anxiety, amyotrophic later sclerosis, Alzheimer's disease, Huntington's disease, Rett syndrome, epilepsy, Parkinson's disease, dementia, diabetic neuropathy, peripheral neuropathy, and central nervous system injuries. Central nervous system injuries include, for example, spinal cord injury, stroke, hypoxia, ischemia, and brain injury.

The methods and compounds as described herein are useful for both prophylactic and therapeutic treatment. For prophylactic use, a therapeutically effective amount of Compound I or derivative thereof as described herein are administered to a subject prior to onset (e.g., before obvious signs of neurological or neuropsychiatric disorder), during early onset (e.g., upon initial signs and symptoms of neurological disorder), or after an established neurological disorder. Prophylactic administration can occur for several days to years prior to the manifestation of symptoms of a disorder, e.g., a neurological or a neuropsychiatric disorder. Prophylactic administration can be used, for example, in the preventative treatment of subjects diagnosed with genetic predisposition or after onset of genetic neurological disorders such as Huntington's disease or prior to surgery in which stroke, hypoxia, or central nervous system injury is a risk. Therapeutic treatment involves administering to a subject a therapeutically effective amount of Compound I or derivative thereof as described herein after a disorder, e.g., a neurological disorder, neuropsychiatric disorder, or metabolic disorder (e.g., obesity), is diagnosed.

Administration of Compound I or derivative thereof as described herein can be carried out using therapeutically effective amounts of Compound I or derivative thereof as described herein for periods of time effective to treat a disorder. The effective amount of Compound I or derivative thereof as described herein may be determined by one of ordinary skill in the art and includes exemplary dosage amounts for a mammal of from about 0.5 to about 200 mg/kg of body weight of active compound per day, which may be administered in a single dose or in the form of individual divided doses, such as from 1 to 4 times per day. Alternatively, the dosage amount can be from about 0.5 to about 150 mg/kg of body weight of active compound per day, about 0.5 to 100 mg/kg of body weight of active compound per day, about 0.5 to about 75 mg/kg of body weight of active compound per day, about 1 to about 70 mg/kg of body weight of active compound per day, about 5 to about 60 mg/kg of body weight of active compound per day, about 10 to about 60 mg/kg of body weight of active compound per day, about 20 to about 60 mg/kg of body weight of active compound per day, about 20 to about 50 mg/kg of body weight of active compound per day, about 50 mg/kg of body weight of active compound per day, about 40 mg/kg of body weight of active compound per day, about 30 mg/kg of body weight of active compound per day, about 20 mg/kg of body weight of active compound per day, about 10 mg/kg of body weight of active compound per day, or about 5 mg/kg of body weight of active compound per day. Those of skill in the art will understand that the specific dose level and frequency of dosage for any particular subject may be varied and will depend upon a variety of factors, including the activity of the specific compound employed, the metabolic stability and length of action of that compound, the species, age, body weight, general health, sex and diet of the subject, the mode and time of administration, rate of excretion, drug combination, and severity of the particular condition.

In these methods, the disorder being treated, e.g., depression, anxiety, central nervous system injury, metabolic disorder (e.g., obesity), or other disorder, can be further treated with one or more additional agents (e.g., an antidepressant, an anti-anxiolytic, an antiviral, or an antibiotic). The one or more additional agents and Compound I or derivative thereof as described herein can be administered in any order, including simultaneous administration, as well as temporally spaced order of up to several days apart. The methods may also include more than a single administration of the one or more additional agents and/or Compound I or derivative thereof as described herein. The administration of the one or more additional agents and Compound I or derivative thereof as described herein may be by the same or different routes and concurrently or sequentially. When treating with one or more additional agents, the Compound I or derivative thereof as described herein can be combined into a pharmaceutical composition with the one or more additional agents. For example, Compound I or derivative thereof as described herein can be combined into a pharmaceutical composition with an antidepressant, such as, for example imipramine, fluoxetine, paroxetine, and/or sertraline. As a further example, Compound I or derivative thereof as described herein can be combined into a pharmaceutical composition with an anti-anxiolytic, such as, for example diazepam, alprazolam, clonazepam, and/or hydroxyzine.

The examples below are intended to further illustrate certain aspects of the methods and compounds described herein, and are not intended to limit the scope of the claims.

EXAMPLES

General Methods
Cells, Reagents, and Mice

Human embryonic kidney 293 (HEK 293) cells were maintained in medium A (DMEM with 10% fetal bovine serum (FBS) and 100 units of penicillin-streptomycin), and DAT (dopamine transporter) stable transfected HEK293 cells were cultured in DMEM with high glucose and L-glutamine (Lonza BioProducts; Basel, Switzerland) containing 10% FBS and 10 U/mL Pen/Strep with 0.4 mg/ml of G418 at 37° C. with 5% $CO_2$ atmosphere in a humidified incubator. Brain-derived neurotrophic factor (BDNF) was obtained from Peptron (Santa Clara, Calif.). Phospho-Akt-473 or 308 and Akt antibodies were from Cell Signaling (Danvers, Mass.). Anti-phospho-Erk1/2, anti-phospho-TrkA Y490, and TrkA and TrkB antibodies were from Santa Cruz Biotechnology, Inc. (Santa Cruz, Calif.). Anti-TrkB antibody was from Biovision (Mountain View, Calif.). Anti-p-TrkA 794 and anti-p-TrkB 816 has been previously described (Rajagopal et al., J. Neurosci., 24:6650-8, 2004; Arevalo et al., Mol. Cell. Biol. 20:5908-16, 2000, which are incorporated herein and in their entirety at least with respect to these antibodies).

[$^3$H]-dopamine, -norepinephrine, and -epinephrine were purchased from New England Nuclear (Boston, Mass.). TrkA$^{F592A}$ and TrkB$^{F616A}$ mice have been described previously (Chen et al., Neuron, 46:13-21, 2005). TrkA$^{F592A}$ and TrkB$^{F616A}$ mice, TrkA +/−, TrkB +/−, TrkC +/−, NET −/− and BDNF +/−C57BL/6 mice were bred in a pathogen-free environment in accordance with Emory Medical School guidelines. Unless otherwise noted, chemicals were purchased from Sigma Aldrich (St. Louis, Mo.).
Cortex-Specific BDNF Deletion The Cortex-Specific Cre mouse line was previously described as "transgenic line C" (Chhatwal et al., Gene Ther., 14:575-583, 2007, which is incorporated herein and in its entirety at least with respect to this mouse line). Briefly, coding sequence for Cre-recombinase (Cre-IRES-DsRed2) was placed downstream of a 3 kb cholecystokinin (CCK) promoter, linearized, purified, and microinjected into the pronuclei of one-cell C57/BL6 embryos, which were then implanted into pseudo-pregnant C57/BL6 females. Following verification of gene expression in the different transgenic lines, the cortex-specific "line C" was crossed to a floxed-stop lacZ reporter mouse line as well as a floxed BDNF mouse line (Chhatwal et al., Nat. Neurosci., 9:870-872, 2006; Soriano, Nat. Genet., 21:70-71, 1999; Rios et al., Mol. Endocrinol., 15:1748-1757, 2001). Region specific Cre gene expression and BDNF deletion were confirmed with in situ hybridization, x-gal staining for beta-galactosidase expression, and Western blot for BDNF protein levels.
Primary Rat Cortical and Hippocampal Neuron Cultures Primary cultured rat cortical neurons were prepared as follows. E17 rat pups were decapitated and cortex was extirpated, cross chopped and suspended by pipetting for separation in 5% fetal calf serum (FCS), 5% horse serum (HS) DMEM. The cell suspension was then centrifuged at 250×g for 5 min. This operation was repeated. Cells were seeded into polyethyleneimine-coated 10 cm$^2$ dishes and 12-well plates including coated-coverslips and incubated at 37° C. in 5% $CO_2$/95% air. After 3 hours, the culture medium was changed to Neurobasal containing B-27 supplement (Invitrogen; Carlsbad, Calif.) and incubated for 4 days. For maintenance, half of the culture medium was changed to fresh Neurobasal/B27 in every 4 days. After 1 week, the dished cultured neurons were ready for use.
Binding Constant Determination Purified TrkA and TrkB ECD or ICD proteins were incubated with different $^3$H-catecholamines at 25° C. for 30 minutes in 1 ml of binding buffer (50 mM Tris-HCl, pH 7.4, 100 mM NaCl, 5 nM $^3$H-catecholamines (32000 cpm)). After the incubation, the reaction mixture was loaded on a Whatman glass-fiber filter (GF-B) (Whatman Inc.; Piscataway, N.J.). The mixture was washed with 3×5 ml washing buffer (50 mM Tris-HCl, pH 7.4). The dried filter paper was put into a small vial and subjected to liquid scintillation counter analysis. The value of the dissociate constant and the number of sites were obtained from Scatchard plots by using the equation $r/[L]free = n/Kd - r/Kd$, where r is the ratio of the concentration of bound ligand to the total protein concentration and n is the number of binding sites.
Catecholamine Uptake in Cultured HEK-293 Cells and Rat Cortical Neurons Uptake was performed on cultured cells in buffer containing 4 mM Tris Base, 120 mM NaCl, 5 mM KCl, 1.2 mM $CaCl_2$, 1.2 mM $MgSO_4$, 5.6 mM glucose, 6.25 mM HEPES, pH to 7.4 with KOH, 1 mM Ascorbate, and 100 nM pargyline (Sigma Aldrich, St. Louis, Mo.). For dopamine (DA) uptake, the cells were incubated for 2 minutes in 1 μM DA (Sigma Aldrich; St. Louis, Mo.) with a 2% tracer of $^3$H-DA (Perkin Elmer; Boston, Mass.). For nonspecific uptake measures, the cells were preincubated with the respective inhibitor for 15 minutes. After uptake, the cells were washed twice with ice-cold buffer to stop the uptake. Cells were then lysed and harvested in 0.1N NaOH. Lysates were added to ScintSafe Econo 1 scintillation fluid (Fisher Scientific; Pittsburgh, Pa.) and allowed to stand overnight in the dark. The subsequent day, samples were read in a LS6500 Beckman Scintillation Counter (Beckman Coulter, Inc.; Fullerton, Calif.). Specific uptake measurements were calculated by subtracting nonspecific uptake from total uptake.
Immunofluorescent Staining Primary hippocampal neurons were seeded on poly-L-lysine coated coverslips in a 12-well plate. After 7 days in vitro, the neurons were treated with 100 ng/ml BDNF or variety of neurotransmitters and 7,8-dihydroxyflavone compound (500 nM) for 30 min, and then washed with PBS. Cells were fixed with 3% formaldehyde in PBS at room temperature for 15 min. The cells were then permeabilized and blocked by 0.4% Triton X-100 and 2% FBS in PBS at room temperature for 15 minutes, washed with PBS three times and treated with anti-MAP2 (1:200) and anti-phospho-TrkB antibodies (1:100). After staining with FITC- or Rhodamine-conjugated secondary antibody, the coverslips were mounted on slides. Fluorescent images were taken by OLYMPUS IX71 fluorescence microscope (Olympus; Center Valley, Pa.).
TrkB F616A Mice Treatment with L-DOPA and DOPS The DOPS concentration was 20 mg/ml, the vitamin C concentration was 2 mg/ml, and the benserazide concentration was 5 mg/ml. The vitamin C prevents oxidation of the DOPS, and the benserazide is a peripheral inhibitor of AADC and restricts the production of NE from DOPS to the brain. The compounds were added to a tube, and 20 µl of 10 M HCl was added to each ml of DOPS solution. The appropriate amount of water was added to the tube, and then HCl was added to achieve the desired volume. For example, to make 1 mL of a DOPS solution, 20 mg DOPS, 2 mg vitamin C, and 5 mg benserazide were added to a tube, followed by 980 µL of water and 20 µL of 10 M HCl. The solution was vortexed until all DOPS was dissolved. The DOPS solution was injected subcutaneously in a volume of 50 µl/g of mouse. The appropriate amount of DOPS solution was pipetted into a clean tube, followed by the amount of 10 M NaOH required to exactly neutralize the HCl. The solution was then shaken. The amount of 10 M NaOH is the weight of the mouse in microliters. For example, for a 20 g mouse, pipet 1 ml of the DOPS solution is pipetted into a tube and 20 µL of 10 M NaOH is added. For a 30 g mouse, 1.5 mL of the DOPS solution is pipetted into a tube and 30 µl of 10 M NaOH is added. Two to four month-old TrkBF616A mice were pretreated with 1NMPP1 in drinking water (50 µM) 1 day before L-DOPA (50 mg/kg) or DOPS (100 mg/kg) intraperitoneal injection. At times of 2 hours and 5 hours after drug administration, the L-DOPA or DOPS-treated mice were sacrificed, respectively. The brain lysates were prepared and analyzed by immunoblotting against anti-phospho-TrkB Y816 and TrkA Y794 antibodies.

Example 1

Figure 2:
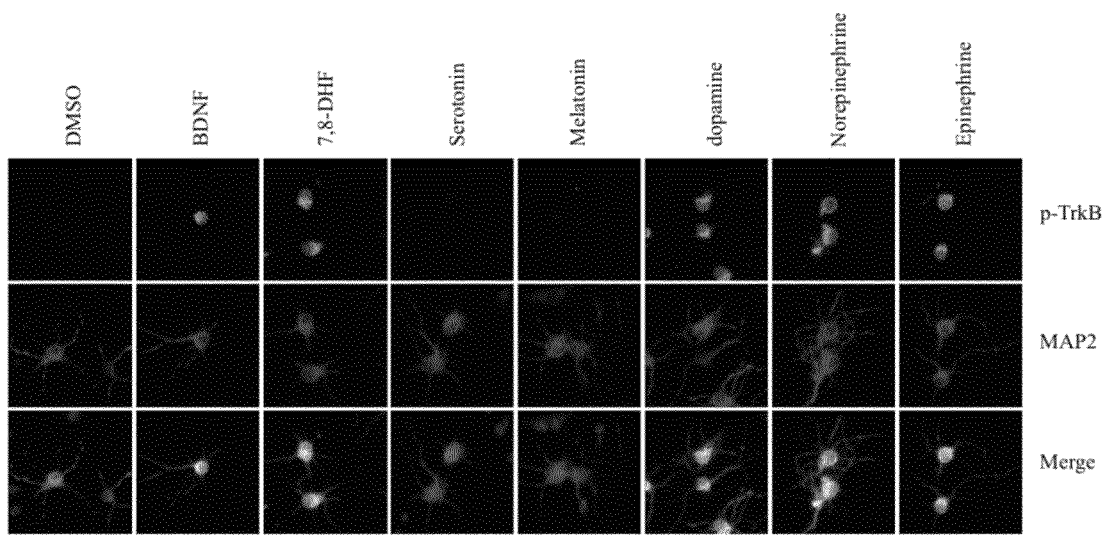
FIG. 2 shows immunofluorescent staining images showing that catecholamines activate TrkB in primary hippocampal neurons.
Figure 3:
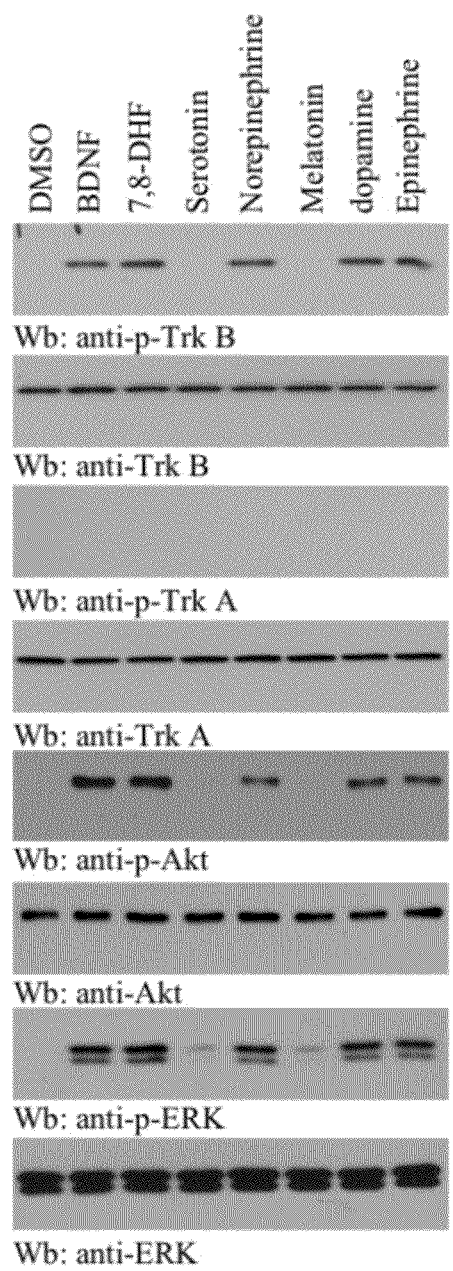
FIG. 3 shows Western blots demonstrating that catecholamines activate TrkB in primary cortical neurons.
Figure 4:
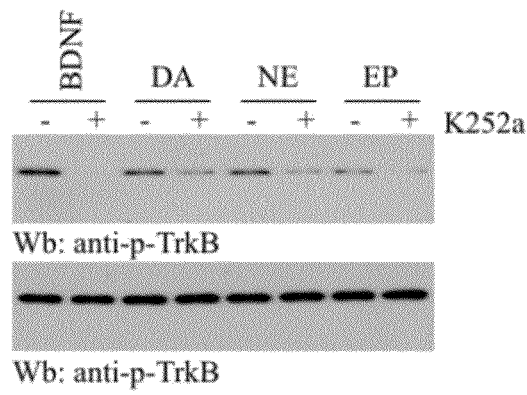
FIG. 4 shows Western blots demonstrating that K252a blocks catecholamines' stimulatory effect on TrkB activation in cortical neurons.
Figure 5:
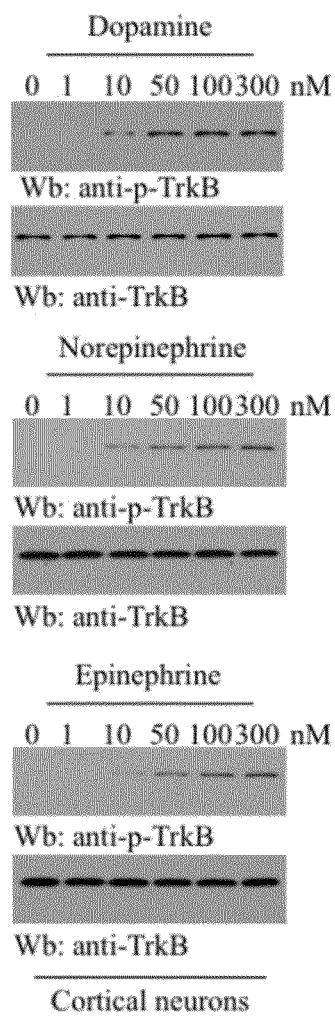
FIG. 5 shows Western blots illustrating the phosphorylation of TrkB in cells treated with increasing concentrations of dopamine, norepinephrine, and epinephrine.
Figure 6:
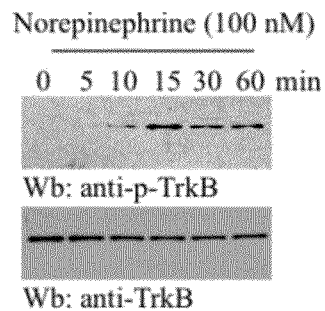
FIG. 6 shows Western blots illustrating the stimulatory effect of 100 nM norepinephrine treatment on TrkB phosphorylation in cortical neurons for increasing amounts of time.

Catecholamines Induce TrkB Activation in Primary Neurons in a Dose-dependent Manner To explore whether monoamine neurotransmitters, including catecholamines (see, e.g., FIG. 1), could stimulate TrkB activation, hippocampal neurons were treated with 300 nM of catecholamines, serotonin, and melatonin for 30 min. Immunofluorescent staining with anti-phospho-TrkB Y816 showed that catecholamines, like BDNF, strongly triggered TrkB tyrosine phosphorylation, whereas serotonin and melatonin did not (FIG. 2). Other serotonin metabolites, including 5-HIAA (5-hydroxyindoleacetic acid) and 5-HT-sulfate, had no effect either. Immunoblotting analysis with the neuronal lysates revealed that TrkB, but not TrkA, was selectively activated by catecholamines. The analysis also showed that TrkB was not activated by serotonin or melatonin. The downstream signaling activation, including Akt and MAPK, correlates with TrkB phosphorylation (FIG. 3). K252a is a selective inhibitor of the tyrosine kinase activity of the Trk family of neurotrophin receptors. K252a pretreatment robustly blocked catecholamine-triggered TrkB tyrosine phosphorylation (FIG. 4), indicating that the stimulatory effect by catecholamines represented Trk receptor-dependent autophosphorylation. To gain the full spectrum of catecholamines' dosage in activating TrkB, cortical neurons were treated with different doses of dopamine, norepinephrine, and epinephrine for 30 min. Catecholamines induced TrkB activation in a dose dependent manner, and demonstrable TrkB phosphorylation was detected when the concentration of catecholamine was as low as 10 nM (FIG. 5). Time course experiments showed that catecholamine-induced TrkB activation started at 10 minutes, peaked at 15 minutes, and sustained at 30-60 minutes, in a kinetic pattern similar to BDNF. Therefore, in the following experiments, catecholamine stimulation time point was set at 15 minutes (FIG. 6). Thus, these data demonstrated that catecholamines, but not serotonin or melatonin, rapidly caused TrkB activation in primary neurons.

Example 2

Figure 7A:
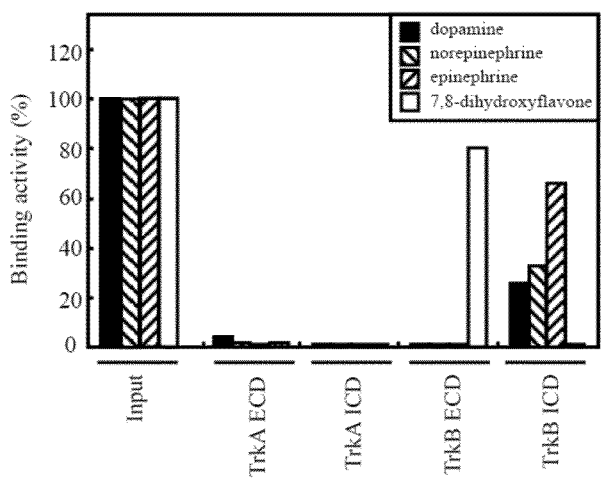
FIGS. 7A and 7B show the results of an in vitro binding assay with purified TrkB and TrkA extracellular domain (ECD) or intracellular domain (ICD) (2 µg) and $^3$H-catecholamines and $^3$H-7,8-dihydroxyflavone.
Figure 7B:
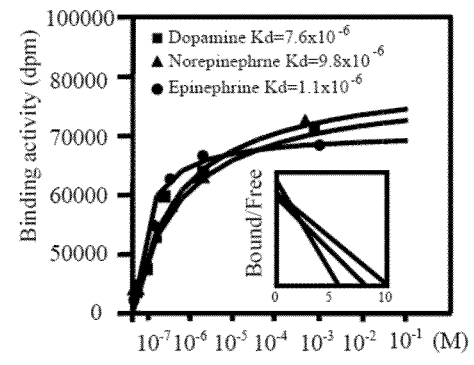
Figure 8:
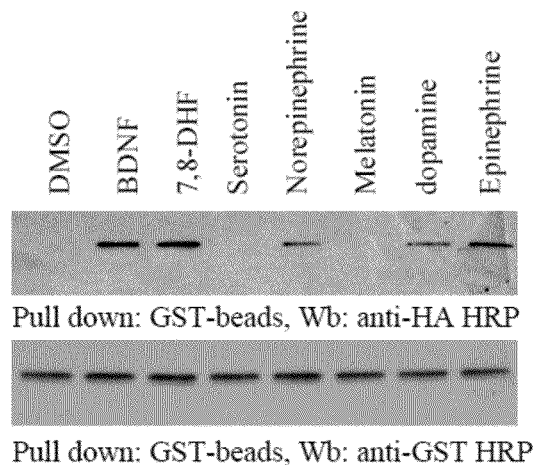
FIG. 8 shows Western blots illustrating that catecholamines cause TrkB dimerization.
Figure 9:
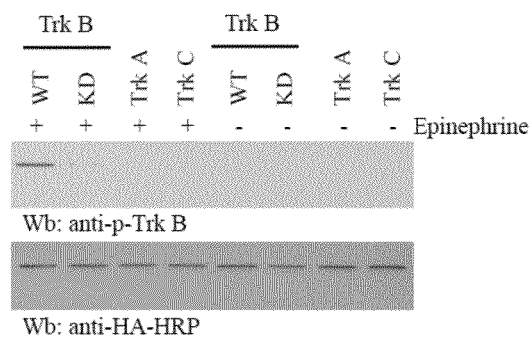
FIG. 9 shows Western blots illustrating that catecholamines induce TrkB autophosphorylation.

Catecholamines Directly Bind the Intracellular Domain of TrkB and Trigger its Dimerization To determine whether catecholamines bind TrkB directly, an in vitro binding assay was conducted with purified ECD (extracellular domain) and ICD (intracellular domain) proteins from Trk receptors and $^3$H-catecholamines. The ICD, but not ECD, from the TrkB receptor bound to catecholamines. Epinephrine exhibited the strongest binding activity. By contrast, the counterparts of TrkA did not bind to $^3$H-catecholamines. As a positive control, 7,8-dihydroxyflavone selectively bound to the ECD of TrkB. Quantitative analysis by Scatchard plot revealed that the TrkB binding constants by dopamine, norepinephrine, and epinephrine were 76 µM, 98 µM, and 1.1 µM, respectively (FIGS. 7A & B). To determine whether the binding by catecholamines to TrkB receptor caused dimerization, GST-TrkB was co-transfected into HEK293 cells with HA-TrkB, followed by BDNF or monoamines treatment for 15 minutes. Co-immunoprecipitation demonstrated that catecholamines, but not serotonin or melatonin, elicited TrkB homodimerization as BDNF (FIG. 8, top panel). Epinephrine elicited tyrosine phosphorylation in TrkB, but not in TrkA or TrkC receptors in transfected HEK293 cells (FIG. 9). In contrast, TrkB-KD (kinase-dead) receptors were not tyrosine phosphorylated. A similar observation was made with dopamine and norepinephrine. These data indicated that tyrosine phosphorylation of TrkB receptor provoked by catecholamines is exerted by the receptor autophosphorylation but not by any other cytoplasmic tyrosine kinases. Hence, catecholamines selectively induced TrkB dimerization and tyrosine autophosphorylation.

To test whether expression of catecholamine transporters enhanced TrkB activation by extracellular catecholamines, HEK293 cells were transfected with DAT (dopamine transporter) or NET (norepinephrine transporter) and treated with various amounts of catecholamines for 5 minutes. In control cells, the minimal required catecholamine to activate transfected TrkB was 100 nM, where 10 nM dopamine was sufficient to activate TrkB in DAT transfected cells. Inclusion of NET in HEK293 cells also substantially enhanced TrkB activation by norepinephrine or epinephrine. Overexpression of NET increased the stimulatory activity approximately 100 fold as compared to control cells, supporting that catecholamine transporters facilitate catecholamines-mediated TrkB activation.

Example 3

Figure 10:
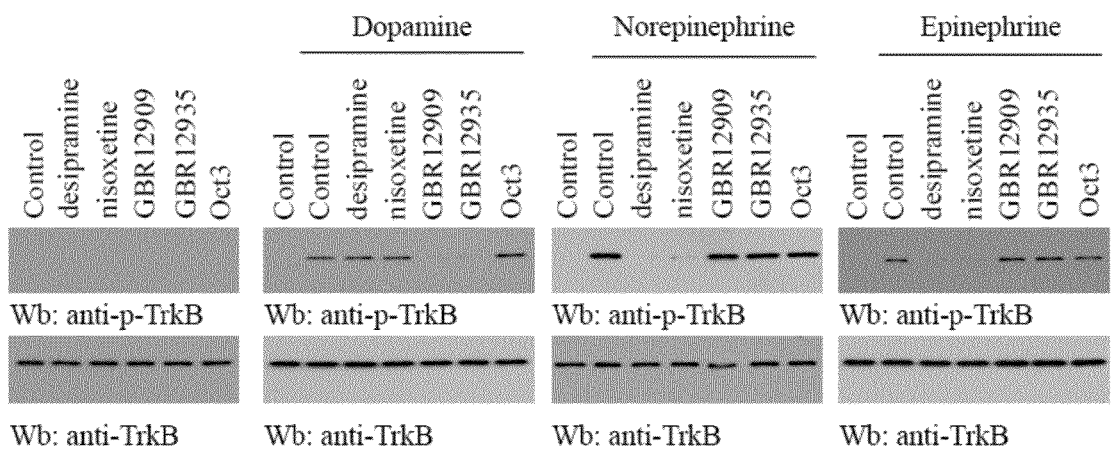
FIG. 10 shows Western blots illustrating that catecholamines activate TrkB in the presence of BDNF antibody in primary cortical neurons.
Figure 11:
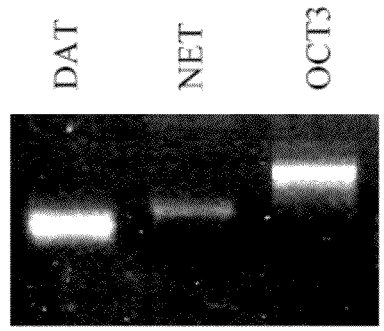
FIG. 11 shows Western blots indicating that NT-3 or NT-4 antibody is unable to block the TrkB agonistic activity of catecholamines.
Figure 12:
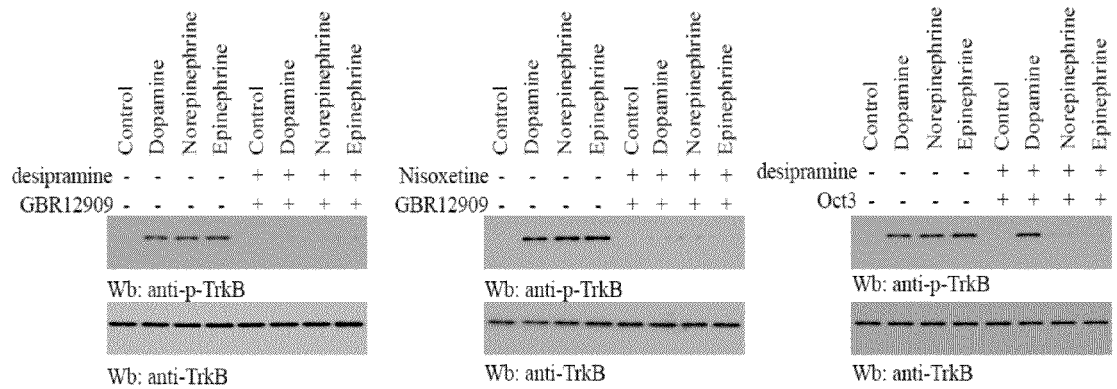
FIG. 12 shows Western blots demonstrating that catecholamines activate TrkB in BDNF null cortical neurons.

Catecholamines Specifically Activate TrkB in Neurotrophins Independent Manner Both antidepressants and exercise increase hippocampal BDNF mRNA expression through enhanced 5-HT and/or NE neurotransmission (Siuciak et al., Pharmacol. Biochem. Behav., 56:131-137, 1997; Dias et al., Neuropharmacology, 45:553-563, 2003; Ivy et al., Pharmacol. Biochem. Behav., 75:81-88, 2003; Garza et al., Pharmacol. Biochem. Behav., 77:209-220, 2004). If catecholamines activated TrkB signaling indirectly by promoting BDNF generation, then scavenging BDNF with its specific antibody would be expected to diminish catecholamines-mediated activation of TrkB. Cultured cortical neurons were pretreated with BDNF-IgG for 30 minutes followed by exposure to BDNF (10 ng/ml) or catecholamines (100 nM) for 15 minutes. Pretreatment with BDNF-IgG abolished BDNF-induced phosphorylation of TrkB; by contrast, BDNF-IgG had no effect on 7,8-dihydroxyflavone or catecholamine-induced phosphorylation of TrkB (FIG. 10), suggesting that the action of catecholamines is independent of BDNF. Likewise, addition of either NT-3 or NT-4 antibody or their combination to primary neuronal cultures failed to prevent or reduce catecholamines-mediated activation of TrkB (FIG. 11). It was then determined whether catecholamines could activate TrkB in neurons cultured from mice carrying a null mutation of BDNF. Addition of catecholamines for 15 min to cortical neurons cultured from BDNF-null mice resulted in evident activation of TrkB as BDNF and 7,8-dihydroxyflavone, whereas serotonin had no effect (FIG. 12).

Figure 13:
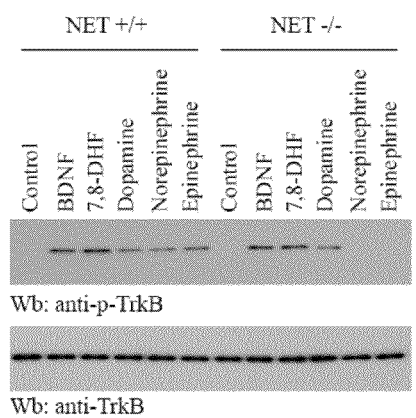
FIG. 13 shows Western blots illustrating that norepinephrine antibody diminishes the TrkB agonistic activity by norepinephrine in cortical neurons.
Figure 14:
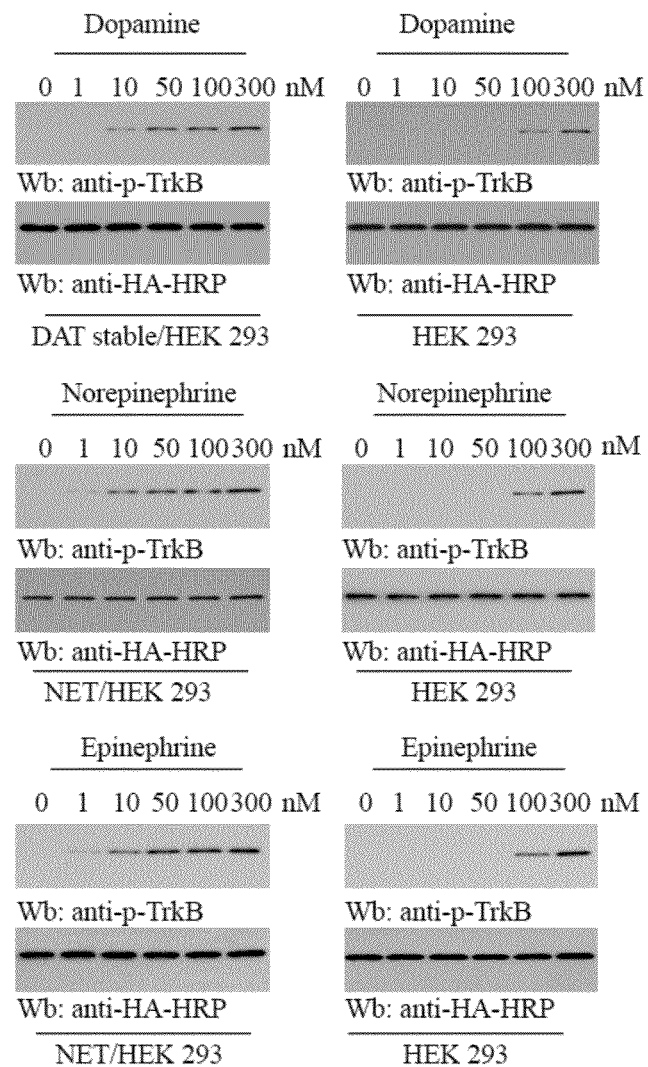
FIG. 14 shows Western blots demonstrating that catecholamines activate TrkB in a catecholamine receptor independent manner.

To further investigate the specificity of catecholamines in inducing TrkB activation, cortical neurons were pretreated with control IgG or norepinephrine IgG, a rabbit polyclonal antibody for norepinephrine, followed by catecholamines. Compared to control IgG, norepinephrine IgG selectively neutralized the agonistic effect of norepinephrine, but not dopamine or epinephrine (FIG. 13). To examine whether the TrkB stimulatory effect by catecholamines is exerted through indirect activation of TrkB by traditional catecholamine receptors, cortical neurons were pretreated with various pharmacological antagonists to dopamine and norepinephrine receptors. Then 100 nM dopamine or norepinephrine was added, respectively. Blockade of dopamine or norepinephrine receptors failed to abrogate TrkB activation by the catecholamines (FIG. 14), indicating that catecholamines do not cause TrkB activation via their G-protein coupled receptors. Therefore, these data support that catecholamines trigger TrkB activation in a catecholamine G-protein receptor independent manner.

Example 4

Catecholamines Selectively Activate TrkB Receptor in Mice

To determine if catecholamines can selectively activate TrkB receptor, cortical neurons were prepared from pups of TrkB +/− mice, which were mated to mice of the same genotype. Catecholamines, but not serotonin, specifically activated TrkB in wild-type but not TrkB—null neurons, whereas TrkA was not activated in either neuron (FIG. 15A, top and $3^{rd}$ panels). Moreover, catecholamines strongly provoked TrkB but not TrkA activation in both wild-type and TrkC knockout neurons (FIG. 15B, top and $3^{rd}$ panel). To further explore whether catecholamines can provoke TrkB activation in vivo, TrkB F616A knock-in mice were employed, where TrkB F616A can be selectively blocked by 1NMPP1 inhibitor and lead to TrkB-null phenotypes.

To assess whether catecholamines can mimic BDNF, cortical neurons were prepared from TrkB F616A knock-in mice and were pretreated with inhibitors K252a or 1NMPP1. As described in Example 1, K252a is a water insoluble, selective inhibitor of the tyrosine kinase activity of the Trk family of neurotrophin receptors, including wild-type TrkB. 1NMPP1 is a water-soluble derivative of K252a and functions as selective inhibitor of mutated TrkB receptors, such as TrkB F616A, but not wild-type TrkB. Catecholamine-provoked TrkB phosphorylation was selectively reduced by 1NMPP1 but not K252a, whereas serotonin had no effect. As a control, TrkA was not activated (FIG. 16, top and $3^{rd}$ panels). Catecholamine-induced TrkB activation in TrkA F592A neurons was robustly inhibited by K252a but not by 1NMPP1. These findings suggest that catecholamines strongly provoked both wild-type TrkB and TrkB F616A tyrosine phosphorylation and activation. Because 1NMPP1 selectively inhibits TrkB F616A activation by catecholamines in vitro, 1NMPP1 may also block TrkBF616A activation by catecholamines in mice. L-DOPA (L-dihydroxyphenylalanine, 50 mg/kg) and DOPS (dihydroxyphenylserine, 100 mg/kg), precursors of dopamine and norepinephrine, respectively, were employed, because dopamine or norepinephrine can not pass through the brain blood barrier. TrkB F616A mice were pretreated with 1NMPP1 (50 µM) before L-DOPA or DOPS administration. As a control, saline and 1NMPP1 had no effect on TrkB tyrosine phosphorylation in mice. As a positive control, 7,8-dihydroxyflavone, L-DOPA and DOPS provoked evident TrkB activation, and pretreatment of 1NMPP1 markedly diminished TrkB activation in F616A mice. Compared to vehicle control, administration of L-DOPA or DOPS into BDNF conditional knockout mice strongly triggered TrkB activation in BDNF −/− cortex. Thus, catecholamines and their precursors strongly and selectively activated TrkB in mice.

Mice lacking dopamine β-hydroxylase (DBH) are unable to synthesize noradrenaline (essential for mouse fetal development) or adrenaline and die in utero. Administration of DOPS, which can be converted to noradrenaline in the absence of DBH, rescued DBH −/− mice from dying. Mature DBH −/− mice can live without supplemental of DOPS. To explore whether exogenously administrated DOPS, which can be changed into norepinephrine and epinephrine, induced TrkB activation in DBH −/− mice, mice were intraperitoneally injected with DOPS and TrkB activation was monitored at different time courses. In wild-type control mice, DOPS induced TrkB activation in a time dependent manner with the maximal effect at 12 hours. In contrast, DOPS-triggered TrkB activation occurred at 1 hour, peaked at 5 hours, and decreased at 12 hours in DBH −/− mice. As a control, TrkA was not activated. Quantitative analysis revealed that BDNF in mouse brain was not significantly altered during the drug treatment. Moreover, L-DOPA and DOPS rapidly induced TrkB activation in primary cultured neurons, indicating that L-DOPA and DOPS directly activate TrkB like catecholamines. Hence, these data demonstrated that catecholamines selectively activate TrkB receptor in mice.

Example 5

Neurotransmitter Transporters Regulate TrkB Activation by Catecholamines

Figure 17:
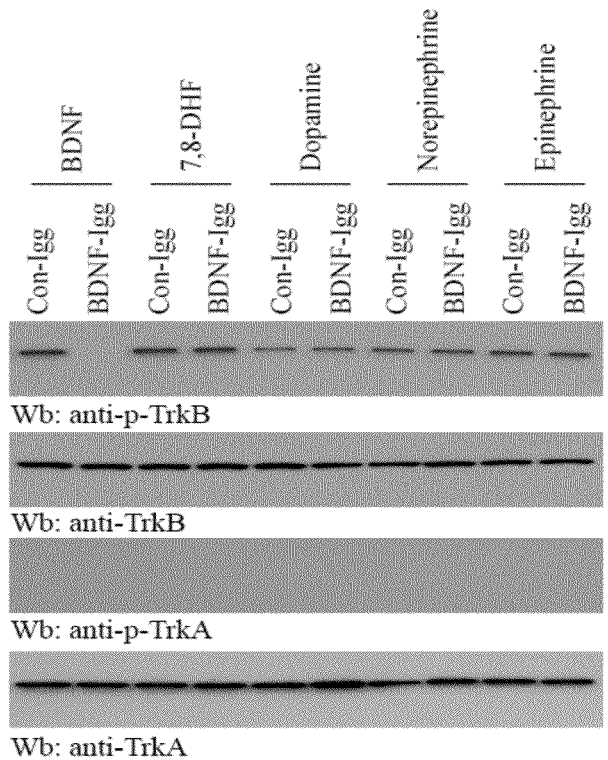
FIG. 17 shows Western blots demonstrating that dopamine transporter and norepinephrine transporter inhibitors block TrkB activation by catecholamines in primary cortical neurons.
Figure 18:
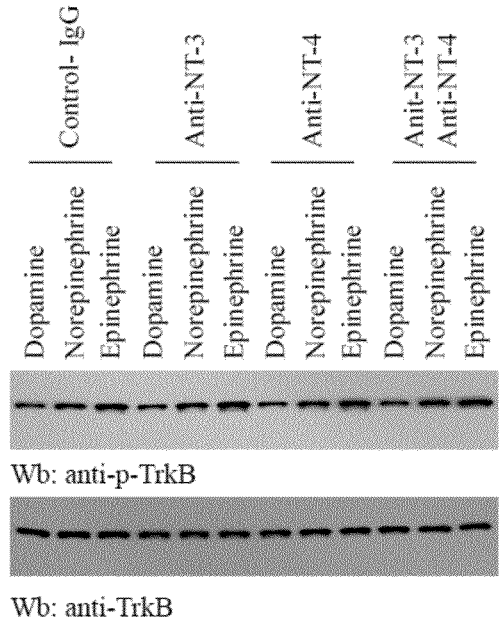
FIG. 18 shows Western blots illustrating that a combination of dopamine transporter and norepinephrine transporter inhibitors suppress TrkB activation by catecholamines.
Figure 19:
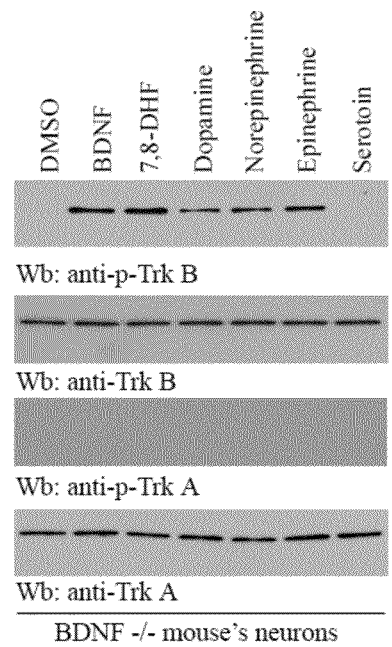
FIG. 19 shows Western blots indicating that norepinephrine transporter depletion blocks TrkB activation by norepinephrine and epinephrine.

To test whether catecholamine transporters are involved in TrkB activation by extracellular catecholamines, cortical neurons were pretreated with various DAT, NET or OCT3 (organic cation transporter 3) inhibitors, followed by dopamine, norepinephrine, and epinephrine treatment. DAT inhibitors GBR 12909 and GBR12935, but not NET inhibitors desipramine or nisoxetine, significantly blocked dopamine-mediated TrkB activation. On the other hand, norepinephrine and epinephrine-provoked TrkB activation was selectively decreased by NET inhibitors but not OCT3 or DAT inhibitors (FIG. 17). Further, the combination of DAT and NET inhibitors robustly repressed TrkB activation in cortical neurons by dopamine, norepinephrine, and epinephrine (FIG. 18), underscoring that catecholamines influx is involved in their agonistic effect on TrkB. It was then determined whether catecholamines could activate TrkB in neurons cultured from mice carrying a null mutation of NET. Addition of dopamine into NET −/− neurons resulted in notable TrkB activation similar to that in wild-type control neurons, whereas norepinephrine or epinephrine-mediated TrkB activation was completely blocked in NET −/− neurons compared to control neurons (FIG. 19). Taken together, these findings demonstrate that catecholamines activating TrkB requires intracellular locale mediated by transporters.

Figure 20:
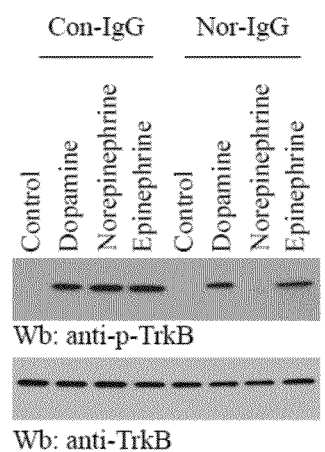
FIG. 20 shows Western blots indicating that norepinephrine antibody selectively blocks the agonistic effect of norepinephrine but not dopamine or epinephrine.

To determine whether the norepinephrine antibody selectively blocks the agonistic effect of catecholamines, rat cortical neurons were pretreated for 15 min with either the control IgG or norepinephrine IgG, a rabbit polyclonal antibody for norepinephrine, followed by 300 nM catecholamines for another 15 min. The cell lysates were analyzed by immunoblotting with anti-p-TrkB-Y-816. Compared with control IgG, norepinephrine IgG selectively inhibited the agonistic effect of norepinephrine but not dopamine or epinephrine on TrkB activation (FIG. 20).

Figure 21:
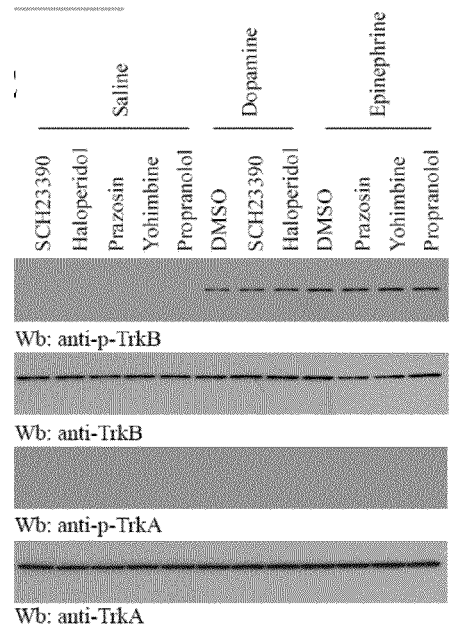
FIG. 21 shows Western blots indicating that dopamine and adrenergic receptor antagonists do not block the agonistic effect of catecholamine on TrkB.

To determine whether dopamine and adrenergic receptor antagonists block the agonistic effect of catecholamines on TrkB, rat cortical neurons were pretreated with various pharmacological antagonists to dopamine and epinephrine receptors for 30 min, followed by 100 nM of dopamine or epinephrine treatment for 15 min, respectively. The pharmacological antagonists to dopamine receptors included SCH23390 (10 μM) and haloperidol (300 nM). The pharmacological antagonists to epinephrine receptors included prazosin (50 nM), yohimbine (10 μM), and propranolol (10 μM). The cell lysates were analyzed by immunoblotting with anti-p-TrkB-Y-816. Both the dopamine and norepinephrine receptor antagonists failed to affect the activation of TrkB by the catecholamines (FIG. 21).

Example 6

OCT3 Inhibitor has No Effect on TrkB Activation by Catecholamines

Figure 22A:
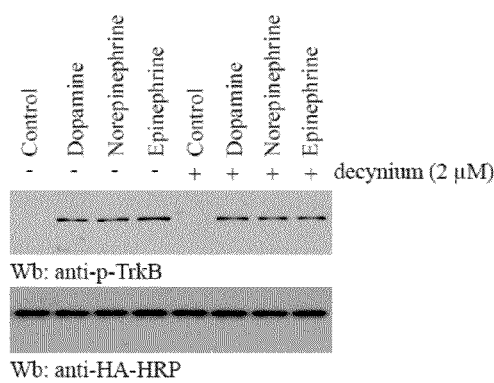
FIG. 22A shows that OCT3 inhibitor has no effect on TrkB activation by catecholamines.

HEK293 cells were transfected with TrkB and pretreated with the OCT3 inhibitor decynium (2 μM) for 30 minutes, followed by stimulation with catecholamines for 15 minutes. The cell lysates were monitored by immunoblotting with anti-p-TrkB-Y-816. The OCT3 inhibitor failed to inhibit the TrkB activation by catecholamines (FIG. 22A, upper panel). An equal amount of TrkB was expressed in each sample (FIG. 22A, lower panel).

Example 7

Figure 22B:
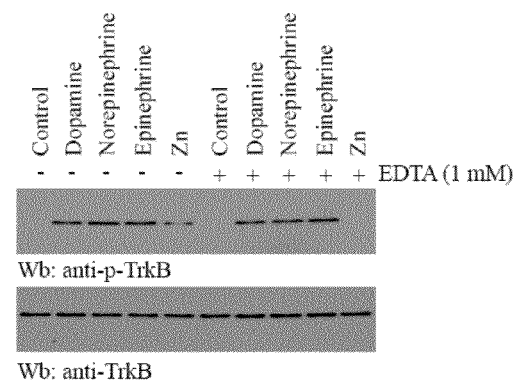
FIG. 22B shows that EDTA blocks the stimulatory effect on TrkB activation by Zn but not catecholamine.

EDTA Blocks the Stimulatory Effect on TrkB Activation by Zn but not Catecholamine A group of primary cortical neurons were pretreated with 1 mM EDTA, and another group of primary cortical neurons were not pretreated. Both groups of primary cortical neurons were then treated with either Zn (100 μM) or a catecholamine (100 nM) for 15 minutes. The neuronal cell lysates were analyzed by immunoblotting with anti-p-TrkB-Y-816 antibody. The stimulatory activity of TrkB activation by Zn, but not catecholamines, was blocked by EDTA (FIG. 22B).

Example 8

Catecholamine Derivatives Orally Activate TrkB Receptor

Catecholamines can directly bind to the kinase domain of the TrkB receptor and activate it. However, the catecholamines are not able to cross through the blood brain barrier. To search for catecholamine derivatives that can pass through the blood brain barrier via oral administration, several compounds containing the catecholamine backbone described herein (Compounds I-2, I-5, I-8, I-9, I-10, I-11, I-17, and I-18) were tested on primary cortical neurons. Cortical neurons (7 DIV cortical neurons from 18 day old Sprague Dawley rat embryos) were treated with 500 nM of the selected compound for 30 min and cell lysates were prepared. The cell lysates (20 mg) were analyzed for TrkB activation by immunoblotting with anti-p-TrkB-Y-816 antibody. Among the tested compounds, Compound I-11 (2-amino-3',4'-dihydroxy-propiophenone) and Compound I-8 (α-dimethylamino-3',4'-dihydroxyacetophenone) prominently activated TrkB (FIG. 23).

To explore whether these compounds could stimulate TrkB in vivo, 50 mg/kg of Compound I-11, Compound I-8, and Compound I-2 (2-(methylamino)-3',4'-dihydroxy-acetophenone) were each orally administered (in saline) to 2-month-old C57BL/6J mice. The mice were sacrificed at different time points and TrkB activation in the brains of the mice was monitored by immunoblotting with anti-p-TrkB-Y-816 antibody. Compound I-11 and Compound I-8 potently activated TrkB 1 to 2 hours after oral administration. The activity escalated with the time course and peaked at 8 hours, suggesting that both compounds are orally bioactive. In contrast, Compound I-2 failed to activate TrkB (FIGS. 24A, 24B, & 24C).

To determine the minimal required dosages for Compound I-11 and Compound I-8, different doses of the compounds were each orally administered to mice. The mice were sacrificed after 4 hours, and the brain lysates were analyzed by immunoblotting with anti-p-TrkB-Y-816 antibody. A titration assay demonstrated that the minimal dosages required for Compound I-11 and Compound I-8 to activate TrkB were 10 mg/kg and 20 mg/kg (FIGS. 25A & 25B). These results indicate that orally administered Compound I-11 and Compound I-8 can pass through the blood brain barrier and activate TrkB receptor in mouse brain.

Example 9

Screening for Catecholamine Derivatives that can Activate TrkB Receptor in Primary Neurons Catecholamine derivatives as described herein, including Compound I-2, Compound I-5, Compound I-7, Compound I-8, Compound I-9, Compound I-10, Compound I-11, Compound I-14, Compound I-15, Compound I-17, Compound I-18, and isoproterenol, were screened for TrkB activation in primary cortical neurons. Cortical neurons (7 DIV cortical neurons from 18 day old Sprague Dawley rat embryos) were treated with 500 nM of the selected compound for 30 min and cell lysates were prepared. The cell lysates (20 mg) were analyzed for TrkB activation by immunoblotting with anti-p-TrkB-Y-816 antibody. The results showed that Compound I-11 (2-amino-3',4'-dihydroxypropiophenone, ADPP) and Compound I-8 (dimethylamino-3',4'-dihydroxyacetophenone, DDAP) displayed prominent stimulatory effect on the TrkB receptor (FIGS. 26A and 26B). As shown in FIG. 26B, Compound I-2, Compound I-7, and Compound I-15 display activity. Taken together, these data support that Compound I-8 and Compound I-11 possess robust TrkB stimulatory effect.

Example 10

Development of Orally Bioactive Catecholamine Derivatives for Activation of TrkB To search for orally bioactive catecholamines, catecholamine derivatives described herein were screened using primary neuronal cultures. The in vitro active compounds, Compounds I-8 and I-11, were adminstered into two to three month old C57BL/6J mice orally, intraperitoneally, and in drinking water. For oral administration, the mice were administered 0 mg (control), 5 mg, 10 mg, 20 mg, or 50 mg of Compound I-8 or Compound I-11. After 4 hours, TrkB phosphorylation in mouse brain was monitored by analyzing the brain lysates using immunoblotting with anti-p-TrkB-Y-816 antibody. The ratios of p-TrK/total TrkB were quantified (FIG. 27A). For intraperitoneal administration, 50 mg/kg of Compound I-8 or Compound I-11 were intraperitoneally injected into the mice. The brain lysates were prepared at different times (0 hr, 1 hr, 2 hr, 4 hr, and 8 hr) and were analyzed by immunoblotting with anti-p-TrkB-Y-816 antibody (FIG. 27B). Compound I-8 and Compound I-11 were dissolved in drinking water and given to mice. After 24 h, the brain lysates were prepared and analyzed by immunoblotting with anti-p-TrkB-Y-816 antibody (FIG. 27C). Compounds I-8 and I-11 were both shown to be orally bio-available catecholamine derivatives that potently suppress neuroexcitotoxin-provoked neuronal cell death in a TrkB-dependent manner. Moreover, these compounds potently activate TrkB in mouse brains when administrated via drinking water or intraperitoneal injection (FIGS. 27A-C). Therefore, these compounds are useful in treating various neurological or neuropsychiatric diseases as described herein.

Example 11

Catecholamine Derivatives Suppress Neuronal Apoptosis

Norepinephrine has neuroprotective activity against oxidative stress-induced neuronal apoptosis. To investigate whether this protective action by norepinephrine is mediated through TrkB, apoptosis of TrkB F616A cortical neurons was monitored. Primary cortical neurons were pretreated with inhibitors K252a or 1NMPP1 followed by overnight treatment with 50 mM glutamate. As shown in FIG. 28A, norepinephrine (NE) robustly suppressed glutamate-provoked neuronal cell death and this protective action was abolished by 1NMPP1 (1NMPP1+NE) but not by K252a (K252a+NE) (apoptosis was quantified using the TUNEL assay). Hence, the neurotrophic activity of NE is TrkB receptor dependent.

To determine whether Compound I-11 (ADPP) and Compound I-8 (DDAP) protect neurons from KA-induced apoptosis, TrkB F616A knockin mice were pretreated with inhibitor 1NMPP1 (16.6 ng/kg) 2 days before the experiment. Compound I-8 (DDAP) or Compound I-11 (ADPP) (50 mg/kg) was orally injected into the mice 2 hours before kainic acid (KA) administration (20 mg/kg). Brain lysates were analyzed by immunoblotting and Caspase-3 ELISA. It was found that oral administration of Compounds I-8 and I-11 robustly repressed kainic acid (KA)-provoked neuronal cell death in mouse brain and 1NMPP1 pretreatment blocked the protective effect (FIG. 28B, left panel). The extent of the protective effect correlates with TrkB activation status by these compounds. Active Caspase-3 ELISA correlated with the immunoblotting results (FIG. 28B, right panel).

Figure 28C:
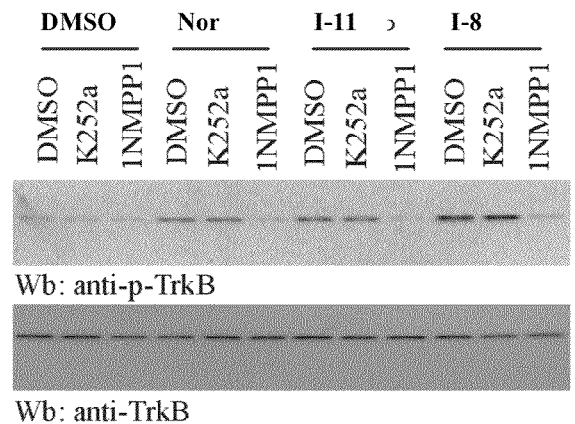
FIG. 28C shows that 1NMPP1, but not K252a, blocks TrkB activation by Compounds I-11 and I-8.

To determine whether Compounds I-8 and I-11 suppress neuronal apoptosis in a TrkB dependent manner, primary cortical neurons were prepared from TrkB F616A knockin mice. On day 7, the primary cortical neurons were pretreated with 100 nM K252a or 1NMPP1 for 30 min, followed by 500 nM ADPP and DDAP. Cell lysates were analyzed by Western blotting. TrkB activation by Compounds I-8 and I-11 in primary TrkB F616A cortical neurons was selectively blocked by 1NMPP1 but not K252a (FIG. 28C). These data demonstrate that catecholamine and its derivatives suppress neuronal cell death through activating TrkB.

Example 12

Catecholamine Derivatives Reveal Potent Antidepressant Effect

Figure 29A:
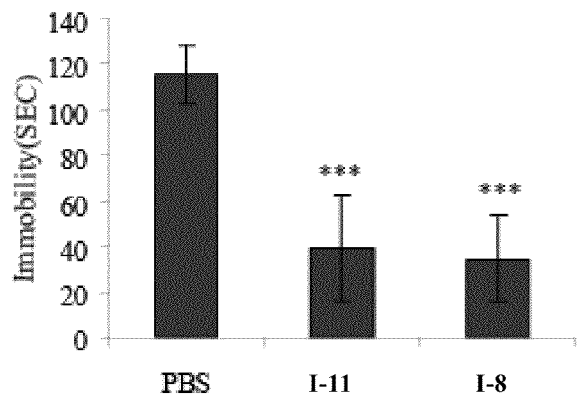
FIGS. 29A and 29B show graphs illustrating the forced swim test results of mice treated with Compound I-11 and Compound I-8.

Accumulating evidence supports that BDNF plays an essential role in mediating antidepressants' therapeutic effects. Infusion of exogenous BDNF into hippocampus or brain stem has antidepressant-like behavioral effect. A forced swim test is broadly used for screening of potential antidepressant drugs and is widely used to measure antidepressant activity. To explore whether Compound I-11 (ADPP) and Compound I-8 (DDAP) have antidepressant effects like BDNF, forced swim tests were conducted. Adult male mice (2-3 months old, n=8) were randomly submitted, without a pre-swim, to a forced swim test of 6 minutes with immobility recorded in the last 4 minutes. Mice were injected intraperitoneally with saline, Compound I-11 (20 mg/kg), or Compound I-8 (20 mg/kg). The mice were allowed to adapt to the test room for 2 days, and the mice were placed in a clear glass cylinder with a diameter of 16 cm, half-filled with clear water at 24° C. The water depth of 14 cm did not allow the mice to reach the bottom of the cylinder, and the water was changed after each mouse. When the mice were treated with Compound I-8 or Compound I-11 (20 mg/kg), the swimming immobility was significantly decreased (see FIG. 29A), suggesting that both compounds imitate BDNF and exert potent anti-depressant effect.

Figure 29B:
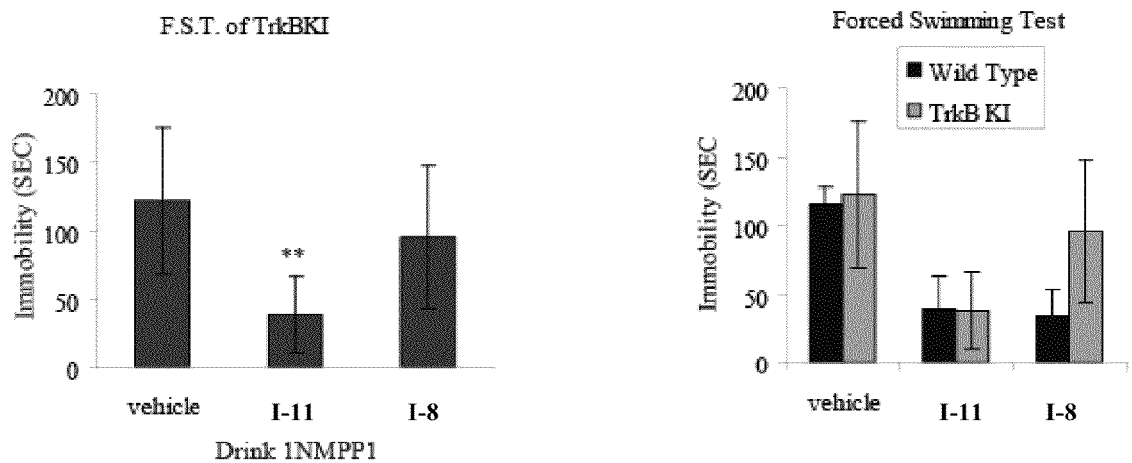

To assess whether the behavior responses caused by catecholamine derivatives is mediated by TrkB receptor, TrkB F616A knockin mice were utilized. The mice were subjected to saline or 1NMPP1 inhibitor pretreatment. No significant difference was observed in the immobility times between the saline and 1NMPP1 treated control groups. In the saline group, both compounds substantially reduced the immobility time; in contrast, Compound I-8 had no significant effect on the immobility time after 1NMPP1 treatment (FIG. 29B), suggesting that inhibition of TrkB signaling cascade blocks the antidepressant effect by Compound I-8. Compound I-11 was still active in decreasing immobility even in the presence of 1NMPP1. These data demonstrate that DDAP mimics BDNF and acts as a potent antidepressant drug in mice through activating TrkB receptor.

The present compounds, compositions, and methods are not limited in scope by the examples described herein, which are intended as illustrations of a few aspects of the compounds, compositions, and methods and any examples that are functionally equivalent are within the scope of the disclosure. Various modifications of the compounds, compositions, and methods in addition to those shown and described herein are intended to fall within the scope of the appended claims. Further, while only certain representative compounds, compositions, methods, and aspects of these compounds, compositions, and methods are specifically described, other compounds, compositions, and methods and combinations of various features of the compounds, compositions, and methods are intended to fall within the scope of the appended claims, even if not specifically recited. Thus a combination of steps, elements, components, or constituents may be explicitly mentioned herein; however, all other combinations of steps, elements, components, and constituents are included, even though not explicitly stated.

What is claimed is:

1. A method of treating Alzheimer's disease in a subject, comprising administering to the subject a therapeutically effective amount of a compound of the following formula:

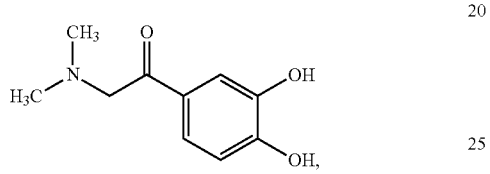

or salts thereof.

* * * * *